United States Patent
Springate et al.

(10) Patent No.: US 11,642,368 B2
(45) Date of Patent: May 9, 2023

(54) HIGHLY PURIFIED AND/OR MODIFIED FUCAN COMPOSITIONS FOR THE TREATMENT OF FIBROUS ADHESIONS

(71) Applicant: ARC Medical Devices Inc., Richmond (CA)

(72) Inventors: Christopher Michael Kevin Springate, Richmond (CA); Ian Millet, Richmond (CA); Sailesh Haresh Daswani, Richmond (CA); Hesong Sun, Richmond (CA); Aileen Shao Ting Yang, Richmond (CA); Hoi Ting Wong, Richmond (CA)

(73) Assignee: ARC Medical Inc., Richmond (CA)

( * ) Notice: Subject to any disclaimer, the term of this patent is extended or adjusted under 35 U.S.C. 154(b) by 0 days.

(21) Appl. No.: 17/260,288

(22) PCT Filed: Jul. 24, 2019

(86) PCT No.: PCT/CA2019/051029
§ 371 (c)(1),
(2) Date: Jan. 14, 2021

(87) PCT Pub. No.: WO2020/019080
PCT Pub. Date: Jan. 30, 2020

(65) Prior Publication Data
US 2021/0290660 A1  Sep. 23, 2021

Related U.S. Application Data

(60) Provisional application No. 62/861,228, filed on Jun. 13, 2019, provisional application No. 62/861,223, filed on Jun. 13, 2019, provisional application No. 62/861,235, filed on Jun. 13, 2019, provisional application No. 62/793,654, filed on Jan. 17, 2019, provisional application No. 62/793,514, filed on Jan. 17, 2019, provisional application No. 62/755,318, filed on Nov. 2, 2018, provisional application No. 62/755,311, filed on Nov. 2, 2018, provisional application No. 62/755,328, filed on Nov. 2, 2018, provisional application No. 62/722,137, filed on Aug. 23, 2018, provisional application No. 62/722,135, filed on Aug. 23, 2018, provisional application No. 62/713,392, filed on Aug. 1, 2018, provisional application No. 62/713,413, filed on Aug. 1, 2018, provisional application No. 62/713,399, filed on Aug. 1, 2018, provisional application No. 62/711,364, filed on Jul. 27, 2018, provisional application No. 62/711,335, filed on Jul. 27, 2018, provisional application No. 62/711,372, filed on Jul. 27, 2018.

(51) Int. Cl.
*A61K 31/737* (2006.01)
*A61P 41/00* (2006.01)
*C08B 37/00* (2006.01)

(52) U.S. Cl.
CPC ............ *A61K 31/737* (2013.01); *A61P 41/00* (2018.01); *C08B 37/0003* (2013.01); *C08B 37/0063* (2013.01)

(58) Field of Classification Search
None
See application file for complete search history.

(56) References Cited

U.S. PATENT DOCUMENTS

| | | |
|---|---|---|
| 5,616,595 A | 4/1997 | Chu et al. |
| 5,772,900 A | 6/1998 | Yorita et al. |
| 6,868,715 B1 | 3/2005 | Carnahan et al. |
| 8,426,381 B2 | 4/2013 | Thibodeau et al. |
| 8,466,125 B2 | 6/2013 | Springate |
| 10,139,378 B2 | 11/2018 | Kang |
| 2003/0224346 A1 | 12/2003 | Karlsson |
| 2004/0014179 A1 | 1/2004 | Thwaites |
| 2007/0122875 A1* | 5/2007 | Sakai ............ C12Y 302/01044 435/69.1 |
| 2007/0298508 A1 | 12/2007 | Deslauriers et al. |
| 2008/0063682 A1 | 3/2008 | Cashman et al. |
| 2009/0105910 A1 | 4/2009 | Hatano et al. |
| 2009/0170801 A1 | 7/2009 | Hao |
| 2009/0170810 A1 | 7/2009 | Hao |
| 2011/0021457 A1 | 1/2011 | Springate |

(Continued)

FOREIGN PATENT DOCUMENTS

| | | |
|---|---|---|
| CA | 2769147 | 2/2011 |
| CN | 1437650 | 8/2003 |

(Continued)

OTHER PUBLICATIONS

Leng, CN107382666A, Nov. 24, 2017, machine translation. (Year: 2017).*

(Continued)

*Primary Examiner* — Layla D Berry
(74) *Attorney, Agent, or Firm* — King IP Law; Joshua King

(57) ABSTRACT

Compositions, methods, systems, etc., are provided for modified and/or purified fucans and corresponding fucan-containing compositions that inhibit fibrous adhesions among other advantages. The purified/modified fucans and fucan compositions have a reduced level of non-fucan components or impurities such as those found in a starting fucan composition. Such reduced undesirable components or impurities include, for example, undesired components bound to the fucan and compounds in the composition that are not a part of or bound to the fucan.

34 Claims, 3 Drawing Sheets

(56) References Cited

U.S. PATENT DOCUMENTS

| | | |
|---|---|---|
| 2011/0172156 A1 | 7/2011 | Dockal et al. |
| 2017/0328873 A1 | 11/2017 | Kang |
| 2018/0051097 A1 | 2/2018 | Springate |

FOREIGN PATENT DOCUMENTS

| | | |
|---|---|---|
| CN | 1985846 | 6/2007 |
| CN | 101011411 | 8/2007 |
| CN | 101037483 | 9/2007 |
| CN | 101156664 | 4/2008 |
| CN | 101659709 | 3/2010 |
| CN | 102665733 | 9/2012 |
| CN | 102911281 | 2/2013 |
| CN | 202778304 | 3/2013 |
| CN | 104586878 | 5/2015 |
| CN | 105399848 | 3/2016 |
| CN | 106176798 | 12/2016 |
| CN | 106832022 | 6/2017 |
| CN | 101037483 | 9/2017 |
| CN | 107155305 | 9/2017 |
| CN | 112513165 | 7/2019 |
| EA | 201270186 | 9/2012 |
| EA | 25808 | 1/2017 |
| EP | 100843 | 2/1984 |
| EP | 0567914 | 11/1993 |
| EP | 1277834 | 1/2003 |
| JP | 10182703 | 7/1998 |
| JP | 2005507077 | 3/2005 |
| JP | 2005508893 | 4/2005 |
| JP | 2005517955 | 6/2005 |
| JP | 2007504273 | 1/2007 |
| JP | 2010519383 | 6/2010 |
| JP | 2013500274 | 1/2013 |
| JP | 2013517285 | 5/2013 |
| JP | 2013180994 | 9/2013 |
| JP | 2014124579 | 7/2014 |
| JP | 2016505083 | 2/2016 |
| JP | 2016128491 | 7/2016 |
| JP | 2017206542 | 11/2017 |
| JP | 2018513383 | 5/2018 |
| KR | 20060031936 | 4/2006 |
| KR | 20060051439 | 5/2006 |
| KR | 20100138440 | 12/2010 |
| KR | 20160011952 | 2/2016 |
| KR | 101950246 | 2/2019 |
| PH | 12012500177 | 10/2012 |
| RU | 2247574 | 3/2005 |
| RU | 2497525 | 11/2013 |
| RU | 2591161 | 7/2016 |
| RU | 2015135635 | 3/2017 |
| RU | 2638859 | 1/2018 |
| WO | WO2008031332 | 3/2008 |
| WO | WO-2008041799 A1 * | 4/2008 ............ A23L 33/10 |
| WO | WO2008103234 | 8/2008 |
| WO | WO2010/110223 | 9/2010 |
| WO | WO2011/011881 | 2/2011 |
| WO | WO2014113836 | 7/2014 |
| WO | WO2016/117599 | 7/2016 |
| WO | WO2017/042603 | 3/2017 |
| WO | WO2017/160739 | 9/2017 |
| WO | WO2020/176989 | 9/2020 |
| WO | WO2020176990 | 9/2020 |

OTHER PUBLICATIONS

Cumashi, Glycobiology vol. 17 No. 5 pp. 541-552, 2007. (Year: 2007).*

Saboural, Mar. Drugs 2014, 12, 4851-4867. (Year: 2014).*

Abstracts of the 25th Annual Meeting of ESHRE, Amsterdam, The Netherlands, Jun. 28, 2009-Jul. 1, 2009.

Ale et al., "Important Determinants for Fucoidan Bioactivity: A Critical Review of Structure-Function Relations and Extraction Methods for Fucose-Containing Sulfated Polysaccharides from Brown Seaweeds," Mar. Drugs, Oct. 24, 2011, vol. 9, pp. 2106-2130.

Baba et al., "Effects of extraction solvent on fucose content in fucoidan extracted from brown seaweed (Sargassum sp.) from Pulau Lankawi, Kedah, Malaysia," AIP Conference Proceedings, Nov. 17, 2016, vol. 1784, 030045, pp. 1-5.

Balboa et al., "Valorization of Sargassum muticum Biomass According to the Biorefinery Concept," Marine Drugs, Jun. 11, 2015, vol. 13, pp. 3745-3760.

Cashman, Johanne et al., "Fucoidan Film Safely Inhibit Surgical Adhesions in a Rat Model," Journal of Surgical Research, vol. 171, pp. 495-603, 2011.

Chen et al., "A new extraction method for fucoidan from the soaked water of brown seaweed (Laminaria japonica)," Desalination and Water Treatment, Feb. 2012, vol. 40:1-3, pp. 204-208.

Chizhov et al., "A study of fucoidan from the brown seaweed Chorda filum," Carbohydrate Research, Jul. 20, 1999, vol. 320, pp. 108-119.

Corrigan, N et al., "Copolymers with Controlled Molecular Weight Distributions and Compositional Gradients through Flow Polymerization," Macromolecules, 2018, vol. 51(12), pp. 4553-4563.

Croci, D.O. et al., "Fucans, but not Fucomannoglucomonas, Determine the Biological Activities of Sulfated Polysaccharides from Liminaria saccharina Brown Seaweed," PLOS ONE, V. 6, I 2, e17283, pp. 1-10, downloaded Sep. 24, 2021, doi.org/10.1371/journal.pone.0017283.

Deniaud-Bouet, E. et al., "Chemical and enzymatic fractionation of cell walls from Fucals: insights into the structure of the extracellular matrix of brown algae," Annals of Botany, May 29, 2014, vol. 114, pp. 1203-1216.

Fernando et al., "A fucoidan fraction purified from Chnoospoora minima: a potential inhibitor of LPS-induced inflammatory responses," International Journal of Biological Macromolecules, 2017, vol. 104, pp. 1185-1193.

Fitton, Janet et al., "Therapies from Fucoidan: An Update" Marine Drugs, vol. 13, No. 9, Sep. 6, 2016, pp. 5920-5946.

Fujikawa, Tatsuo et al., "Occurrence of Fucoidan and Fucoidan Analogues in Brown Seaweed," Agricultural Chemistry, vol. 49, No. 9, 1975, pp. 455-461.

Greco et al., "A Simple and Effective Method for High Quality Co-Extraction of Geonomic DNA and Total RNA from Low Biomass Ectocarpus siliculosus, the Model Brown Alga," PLOS One, May 27, 2014, vol. 9(5), pp. 1-13.

"Guidance for Industry, Estimating the Maximum Safe Starting Dose in Initial Clinical Trials for Therapeutics in Adult Healthy Volunteers," U.S. Department of Health and Human Services Food and Drug Administration Center for Drug Evaluation and Research (CDER), 2005, pp. 1-27.

Hahn et al., "Novel Procedures for the extraction of fucoidan from brown algae," Process Biochemistry, Jun. 23, 2012, vol. 47, pp. 1691-1698.

Haroun-Bouhedja et al., "Relationship between Sulfate Groups and Biological," Thrombosis Research, Dec. 1, 2000, vol. 100(5), pp. 453-459.

Hoagland, "The Complex Carbohydrates and Forms of Sulphur in Marine Algae of the Pacific Coast," The Journal of Biological Chemistry, 1915, vol. 23(1), pp. 287-297.

International Search Report and Written Opinion relating to International Patent Application No. PCT/CA2019/051026, dated Oct. 16, 2019, 17 pages.

International Search Report and Written Opinion relating to International Patent Application No. PCT/CA2019/051027, dated Nov. 20, 2019, 15 pages.

International Search Report and Written Opinion relating to International Patent Application No. PCT/CA2019/051030, dated Nov. 27, 2019, 24 pages.

International Search Report and Written Opinion relating to International Patent Application No. PCT/CA2019/051028, dated Nov. 15, 2019, 27 pages.

International Search Report and Written Opinion relating to International Patent Application No. PCT/CA2019/051029, dated Dec. 12, 2019, 15 pages.

International Search Report and Written Opinion relating to International Patent Application No. PCT/CA2020/050294, dated May 29, 2020, 8 pages.

(56) References Cited

OTHER PUBLICATIONS

International Search Report and Written Opinion relating to International Patent Application No. PCT/CA2020/050295, dated Jun. 5, 2020, 12 pages.
Kim, et al., "Molecular weight and sulfate content modulate the inhibition of a-amylase by fucoidan relevant for type 2 diabetes management," PharmaNutrition, Jul. 2015, vol. 3(3), pp. 108-114.
Kopplin, Georg et al., "Structural Characterization of Fucoidan from Laminaria hyperborean: Assessment of Coagulation and Inflammatory Properties and Their Structure-Fucan Relationship," Applied Bio Materials, 2018, vol. 1. pp. 1880-1892.
Koyanagi et al., "Oversulfation of Fucoidan Enhances its Anti-Angiogenic and Anti-Tumor Activities," Biochemical Pharmacology, Jan. 15, 2003, vol. 65(2), pp. 173-179.
Lee et al., "Variation in Fucoidan Contents and Monosaccharide Compositions of Korean Undaria pinnatifida (Harvey) Surigar (Phaephyta)," Algae, vol. 21:1, 2006, 157-160.
Li et al., "Fucoidan: Structure and Bioactivity," Molecules, Aug. 12, 2008, vol. 13, pp. 1671-1695.
Ly et al., "Studies on Fucoidan and its Production from Vietnamese Brown Seaweeds," ASEAN Journal on Science and Technology for Development, 2005, vol. 22(4), pp. 371-380.
Mabeau, Serge et al., "Fractionation and Analysis of Fucans from Brown Algae", Phytochemistry, vol. 29, No. 8, pp. 2441-2445, 1990.
Makarenkova, I D et al., "Sulfated polysaccharides of brown seaweeds are ligands of toll-like receptors," Biochemistry (Moscow) Supplement Series B: Biomedical Chemistry, SP Maik Nauka, Interperiodica, Dordrecht, vol. 6, No. 1, Mar. 2012, pp. 75-80.
Men'Shova, R.V. et al., "Effect of pretreatment conditions of brown algae by supercritical fluids on yield and structural characteristics of fucoidans," Chemistry of Natural Compounds, Jan. 2013, vol. 48, No. 6, pp. 923-926.
Mulloy, Barbara et al., "Sulfated fucans from Echinoderms have a regular tetrasaccharide repeating unit defined by specific patterns of sulfation at the 0-2 and 0-4 positions Analysis View project," Oct. 1, 1994, DOI: 10.1016/S0021-9258 (17) 31763-5.
Nishino, Takashi et al., "Anticoagulant and antithrombin activities of oversulfated fucans," Carbohydrate Research, 229 (1992) 355-362.
Pereira, M.S. et al., "Is there a correlation between structure and anticoagulant action of sulfated galactans and sulfated fucans," Glycobiology, Oct. 1, 2002, vol. 12(10), pp. 573-580, downloaded from the internet https://doi.org/10.1093/glycob/cwf077.
Qiu et al., "Effect of oversulfation on the chemical and biological properties of fucoidan," Carbohydrate Polymers, Nov. 21, 2005, vol. 63, pp. 224-228.
Regis et al., "Regioselective desulfation of sulfated L-fucopyranoside by a new sulfoesterase from the marine mollusk Pecten maximus Application to the structural stud of agal fucoidan (*Ascophyllum nodosum*)," European Journal of Biochemistry, Aug. 19, 2003, vol. 268, pp. 5617-5626.
Sabboural, P. et al. "Purification of a Low Molecular Weight Fucan for SPECT Molecular Imaging of Myocardial Infarction,", Marine Drugs 2014, vol. 12, pp. 4851-4867.
Sakai, Takeshi et al., Polymers, Jul. 2006, vol. 55, pp. 488-489.
Seimon, T.A. et al., "Combinational pattern recognition receptor signaling alters the balance of life and death in macrophages," PNAS Cell Biology (2006), vol. 103, No. 52, pp. 19794-19799.
Sezer, A.D. et al., "Preparation of fucoidan-chitosan hydrogel and its application as burn healing accelerator on rabbits," Biol Pharm Bull. 2008, vol. 31(12), pp. 2326-2333.
Simurant et al., "Purification and Characterization of Fucoidan From the Brown Seaweed Sargassum binderi sonder," Squalen Bulletin of Marine & Fisheries Postharvest & Biotechnology, Aug. 2015, vol. 10(2), pp. 79-87.
Soeda et al., "Preparation of oversulfated fucoidan fragments and evaluations of their antithrombotic activities," Thrombosis Research, Nov. 1, 1993, vol. 72(3), pp. 247-256.
Soeda et al., "Oversulfated fucoidan and heparin suppress endotoxin induction of plasminogen activator inhibitor-1 in cultured human endothelial cells: their possible mechanism of action," Biochimica et Biophysica Acta (BBA)—Molecular Cell Research, Oct. 19, 1995, vol. 1269(1), pp. 89-90.
Usui et al., "Isolation of Highly Purified Fucoidan from Eisenia bicyclis and Its Anticoagulant and Antitumor Activities," Agric. Biol. Chem, Mar. 12, 1980, vol. 44(8), pp. 1965-1966.
Wang, "Impacts of Processing and Storage Methods on the Yield and Composition of Fucoidan from Undaria pinnatifida," Auckland University of Technology, Nov. 2014, pp. 1-71.
Wijesinghe et al., "Biological activities and potential industrial applications of fucose rich sulfated polysaccharides and fucoidans isolated from brown seaweeds: A review," Carbohydrate Polymers, Dec. 24, 2011, vol. 88. pp. 13-20.
Wu et al., "Liquid-Liquid Extraction of Fucoidan Leached from Brown Seaweeds," The Chinese Journal of Process Engineering, Feb. 2002, ISSN http://en.cnki.com.cn/Article_en/CJFDTotal-HGYJ200202006.htm.
Wu, "Solvent Extraction of Fucoidan in Aqueous Solution with Quaternary Ammonium Salt as Extractant," Chinese High Technology Letters, Aug. 2001, ISSN http://en.cnki.com.cn/Article_en/CJFDTotal-GJSX200108009.htm.
Wu et al., "Structural Analysis and Anticoagulant Activities of the Novel Sulfated Fucan Possessing a Regular Well-Defined Repeating Unit from Sea Cucumber," Marine Drugs, Apr. 13, 2015, vol. 13, p. 2063-2084.
Xing et al., "Extraction and Separation of Fucoidan from Laminaria japonica with Chitosan as Extractant," Hindawi Publishing Corporation, 2013, pp. 1-4.
Zayed et al., "Physiochemical and Biological Characterization of Fucoidan from Fucus vesiculosus Purified by Dye Affinity Chromatography," Marine Drugs, Apr. 15, 2016, vol. 14(4), pp. 1-15.
Zhang, H. et al., "Control of molecular weight distribution for polypropylene obtained by commercial Ziegler-Natta catalyst: effect of temperature," Polym. Bull. 2011, vol. 67, pp. 1519-1527.
Zhao, Yu et al., "Fucoidan Extracted from Undaria pinnatifida: Source for Nutraceuticals/Functional Foods," Marine Drugs, 2018, vol. 16: 321, 17 pages.
Zhao et al., "The Removal of Lead from Purified Fucoidan Extracted from Kelp Laminari japonica," Fisheries Science, Feb. 2012, ISSN http://en.cnki.com.cn/Article_en/CJFDTOTAL-CHAN201202011.htm.

* cited by examiner

Base-treated
Sample B

Unmodified
Sample A

HIGHLY PURIFIED AND/OR MODIFIED FUCAN COMPOSITIONS FOR THE TREATMENT OF FIBROUS ADHESIONS

CLAIM FOR PRIORITY

The present application claims the benefit of U.S. provisional patent application No. 62/711,364, filed Jul. 27, 2018; U.S. provisional patent application No. 62/711,372, filed Jul. 27, 2018; U.S. provisional patent application No. 62/711,335, filed Jul. 27, 2018; U.S. Provisional Patent Application Ser. No. 62/713,399, filed Aug. 1, 2018; U.S. provisional patent application No. 62/722,135, filed Aug. 23, 2018; U.S. provisional patent application No. 62/755,311, filed Nov. 2, 2018; U.S. provisional patent application No. 62/793,514, filed on Jan. 17, 2019; U.S. provisional patent application No. 62/861,223, filed Jun. 13, 2019; U.S. Provisional Patent Application Ser. No. 62/713,392, filed Aug. 1, 2018; U.S. provisional patent application No. 62/713,413, filed Aug. 1, 2018; U.S. provisional patent application No. 62/722,137, filed Aug. 23, 2018; U.S. provisional patent application No. 62/755,318, filed on Nov. 2, 2018; U.S. provisional patent application No. 62/861,228, filed Jun. 13, 2019; U.S. Provisional Patent Application Ser. No. 62/755,328, filed Nov. 2, 2018; U.S. provisional patent application No. 62/793,654, filed Jan. 17, 2019; and, U.S. provisional patent application No. 62/861,235, filed Jun. 13, 2019, all of which applications are incorporated herein by reference in their entirety.

BACKGROUND

Fucans (including fucoidan) are sulfated polysaccharides. In general terms, this means that they are molecules made up of a number of sugar groups, and also have sulfur atoms attached to the sugar groups. The main sugar group is called "fucose", which is sugar that has 6 carbon atoms and has the chemical formula $C_6H_{12}O_5$. "Fucoidan" (or fucoidin) indicates fucans derived from brown algae (seaweed). Fucans can exist alone, or in a mixture of other sugars, for example in a mixture of sugars such as xylose, galactose, glucose, glucuronic acid and/or mannose. These other sugars can be extracted from the seaweed or other source with the fucan. Although fucans are currently derived from natural sources such as the brown algae (seaweeds), sea cucumbers, etc., mentioned herein, "fucan" includes polymer molecules having the chemical and structural motifs of the fucans as discussed herein regardless of the ultimate source(s) of the fucans.

Fucoidan can be obtained from a variety of species of brown algae including but not limited to: *Adenocystis utricularis, Ascophyllum nodosum, Chorda filum, Cystoseirabies marina, Durvillaea antarctica, Ecklonia kurome, Ecklonia maxima, Eisenia bicyclis, Fucus evanescens, Fucus vesiculosis, Hizikia fusiforme, Himanthalia Elongata, Kjellmaniella crassifolia, Laminaria brasiliensis, Laminaria cichorioides, Laminaria hyperborea, Laminaria japonica, Laminaria saccharina, Lessonia trabeculata, Macrocystis pyrifera, Pelvetia fastigiata, Pelvetia Canaliculata, Saccharina japonica, Saccharina latissima, Sargassum stenophylum, Sargassum thunbergii, Sargassum confusum, Sargassum fusiforme* and *Undaria pinnatifida*. These exemplary species are all from the taxonomic class Phaeophyceae and the majority of these species fall into the families of Fucales and Laminariaceae.

Fucans including fucoidan have been shown to be efficacious in serving as a barrier device to prevent, inhibit, and treat the formation of fibrous adhesions. They have also found use in the treatment of other related diseases and conditions.

Thus, there has gone unmet a need for the preparation of purified fucans including such fucans being modified to have desired molecular weight distributions and/or sulfate levels. The present compositions, systems and methods, etc., provide these and/or other advantages.

SUMMARY

Compositions, methods, systems, etc., are provided for fucans and fucan-containing compositions that inhibit fibrous adhesions among other advantages. The fucans and fucan compositions herein comprise fucans, including purified/modified fucans, having particular levels of desired, specified fucan components. The body of this application often refers to purified/modified fucans and purified/modified fucan compositions; such references include all fucans/fucan compositions herein except in the claims or unless clearly limited to purified/modified fucans/purified/modified fucan compositions from the context. In some embodiments, the fucans and compositions containing them are suitable for medical and surgical applications. The fucans and fucan compositions have a reduced level of non-fucan components or impurities such as those found in a feedstock fucan composition. Such undesirable components or impurities include, for example, undesired components that are bound to the fucan (e.g., ionic, covalent, hydrogen bonding, etc.) and compounds in the composition that are not a part of or chemically and/or ionically bound to the fucan. The undesired fucan components can be quantified in comparison (e.g., w/w) to the fucan. The non-fucan compounds and undesired fucan components may hereafter collectively be referred to as impurities of the fucan and/or of the compositions comprising the fucan herein. These purified/modified fucans can, for example, reduce dangerous complications during the medical and surgical use of fucans due to impurities.

The present compositions, methods, systems, etc., provide compositions comprising desired fucans, including purified/modified fucans obtained from starting or initial fucan compositions (i.e., fucan compositions from which the purified/modified fucans can be derived; such starting fucan compositions may or may not be crude or have been previously processed, such as a feedstock fucan composition) as well as methods of obtaining such desired purified/modified fucans and methods of use of such purified/modified fucans.

In some aspects, the present systems, devices and methods, etc., provide compositions comprising fucans comprising a total content of fucose, galactose, sulfate and counterions of greater than 90% w/w, 92% w/w, 94% w/w, 95% w/w, 97% w/w, 97.5% w/w, 98%, 98.8%, 99%, 99.5%, or 99.9% w/w. In some embodiments, the fucose content can be greater than 25% w/w, 30% w/w, 35% w/w; the galactose content can be less than 10% w/w or 5% w/w. The total counterion content can be less than 17% w/w or 14% w/w. The counterion can be a pharmaceutically acceptable counterion, such as aluminum, arginine, benzathine, chloroprocaine, choline, sodium, potassium, lithium, ammonium, ethylene diamine, diethylamine, diethanolamine, ethanolamine, histidine, lysine, N-methyl glucamine, meglumine, procaine, triethylamine, zinc, calcium and magnesium. In some embodiments the counterion can comprise, consist of, or consist essentially of at least one of sodium and potassium.

In certain embodiments, the provide compositions comprising the purified/modified fucans can comprise a total fucose, galactose and sulfate content of greater than 75% w/w, 80% w/w, 84% w/w. At least 60% w/w of the molecular weight distribution can be greater than 100 kDa, a weight average molecular weight greater than 100 kDa, and/or peak molecular weight greater than 70 kDa. One exemplary approach for determining such distribution is to use an aqueous gel permeation chromatography set up comprising or consisting essentially of:

one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;

a refractive index detector at about 30° C.;

0.1M sodium nitrate mobile phase run at 0.6 mL/min; and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa. The peak molecular weight standard curve further can comprise a dextran standard with a peak molecular weight between about 3 kDa and about 5 kDa.

The provide compositions comprising the fucans can have a number average molecular weight greater than 50 kDa, a sulfation level of between 20% w/w and 60% w/w or between 30% w/w and 55% w/w or 35% w/w and 52% w/w.

The total carbohydrate content can be between 27% w/w and 80% w/w. The total fucose content as a percentage of the total carbohydrate content can be at least about 30% w/w, 50% w/w, 70% w/w, 90% w/w or 95% w/w. The total galactose content as a percentage of the total carbohydrate content can be below about 60% w/w or 20% w/w. The total of glucuronic acid, mannose, rhamnose, glucose and xylose content as a percentage of the total carbohydrate content can be below about 30% w/w.

Also provided herein are methods comprising making or using the provide compositions comprising the purified/modified fucans herein. The using can comprise treating fibrous adhesions.

In some embodiments, the fucan compositions herein include solid fucan compositions, and comprise at least 90% w/w fucans, such as purified/modified fucans herein, the solid fucan composition further comprising a total water content of less than 7% w/w, 6% w/w, 5% w/w, 4% w/w, 3% w/w, 2% w/w, 1% w/w or 0.1% w/w.

In certain embodiments, the compositions herein are medically acceptable fucan compositions comprising a therapeutically effective amount of the purified/modified fucans herein in a medically acceptable buffer or diluent. The methods herein include treating a fibrous adhesion in an animal such as a human comprising selecting purified/modified fucans herein to inhibit the fibrous adhesion and administering a therapeutically effective amount of the composition or the fucan within the composition at a dosage range between 0.5 mg/kg and 50 mg/kg compositions herein to the site of a wound of the animal. The dosage range can also be between 1 mg/kg and 25 mg/kg. Methods can also comprise use of a dosage range comprising between 0.5 mg/kg and 50 mg/kg, or between 1 mg/kg and 25 mg/kg, to treat a targeted disease or disorder, including for example fibrous adhesions.

Also provided herein are methods of making the compositions comprising purified/modified fucans herein including, for example, methods for removing impurities from a starting fucan composition, such as a feedstock fucan composition, to obtain purified/modified fucans. Such methods can comprise, for example:

providing a starting fucan composition comprising impurities;

adding a flocculation aid to the starting fucan composition to produce a reaction mixture;

flocculating the impurities by heating the reaction mixture to produce flocculated impurities; and removing the flocculated impurities.

Providing the starting fucan compositions can comprise providing the starting fucan compositions as a solution, and the methods further can comprise collecting the purified/modified fucans in a reduced-impurities solution. The flocculating the impurities can comprise heating the reaction mixture in excess of atmospheric pressure, and the flocculation aid can comprise a salt, such as chloride, bromide, iodide, fluoride, sulfate, sulfite, carbonate, bicarbonate, phosphate, nitrate, nitrite, acetate, citrate, silicate and/or cyanide of an alkali metal, alkaline earth metal, aluminum and/or ammonium. The flocculation aid can comprise a base such as hydroxide and/or oxide of an alkali metal, alkaline earth metal, aluminum and/or ammonium.

The impurities removed comprise at least one of particulates, lipids, fatty acids, phlorotannins, laminarins, alginates, proteins, Maillard reaction products, fucoxanthin, chlorophyll, bacteria, cellular components and DNA.

Additional methods for removing impurities from starting fucan compositions to obtain purified/modified fucans can comprise:

providing starting fucan compositions as a solid and an extraction media incapable of dissolving fucans, configured for dissolving impurities;

mixing the starting fucan compositions with the extraction media to produce a mixture of the purified/modified fucans and the extraction media; and separating the purified/modified fucans from the extraction media.

The methods can further comprise collecting the compositions comprising the purified/modified fucans as a solid. The extraction media can comprise at least one organic solvent with a relative polarity less than 0.765. The values for relative polarity can be normalized from measurements of solvent shifts of absorption spectra. See for example Christian Reichardt, Solvents and Solvent Effects in Organic Chemistry, Wiley-VCH Publishers, 3rd ed., 2003. The organic solvent can comprise at least one of ethanol, isopropanol, methanol, benzene, diethyl ether, decamethylcyclo-pentasiloxane, ethyl acetate, butanol, hexane, heptane, heptanol, octanol and decanol. The extraction media further can comprise at least one of a base, a detergent and an oxidizing agent. Providing the starting fucan compositions in a solid form can comprise precipitating the starting fucan compositions from a solution. The impurities removed can comprise at least one of particulates, lipids, fatty acids, phlorotannins, laminarins, alginates, proteins, Maillard reaction products, fucoxanthin, chlorophyll, bacteria, cellular components and DNA.

Further methods for removing impurities from starting fucan compositions to obtain purified/modified fucans can comprise:
    providing starting fucan compositions comprising impurities, including suspended impurities in a solution;
    precipitating the impurities from the solution using an ionic-multivalent impurity precipitant, thereby producing a mixture of suspended impurities, precipitated impurities and a supernatant solution; and
    separating the suspended impurities and precipitated impurities from the supernatant solution.
The methods can also comprise collecting the supernatant solution comprising the compositions comprising the purified/modified fucans.

The ionic-multivalent impurity precipitant can comprise a salt of a divalent or trivalent cation; the salt can be a chloride, bromide, iodide, fluoride, sulfate, sulfite, carbonate, bicarbonate, phosphate, nitrate, nitrite, acetate, citrate, silicate and/or cyanide. The cation can be an alkaline earth metal, zinc, aluminum, copper and/or iron. The ionic-multivalent impurity precipitant can comprise a base of a divalent or trivalent cation. The base can be a hydroxide and/or oxide of an alkaline earth metal, zinc, aluminum, copper and/or iron.

The separating the suspended impurities and precipitated impurities from the supernatant solution can further comprise flocculating the suspended impurities and precipitated impurities by adding a flocculant to the mixture of suspended impurities, precipitated impurities and supernatant solution. The flocculant can comprise at least one of potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminoethyl acrylate methyl chloride; N,N-dimethylaminoethyl methacrylate methyl chloride quaternary; and polydiallyldimethyl-ammonium chloride. The methods further can comprise maintaining a pH of between about 7 and 14. Maintaining the pH can comprise the addition of base. The impurities removed can comprise at least one of particulates, lipids, fatty acids, phlorotannins, laminarins, alginates, proteins, Maillard reaction products, fucoxanthin, chlorophyll, bacteria, cellular components and DNA.

Methods for removing impurities from starting fucan compositions to obtain purified/modified fucans can comprise:
    providing starting fucan compositions comprising impurities;
    adjusting the starting fucan compositions pH to between about 8 and 14;
    adding to the starting fucan compositions a cellular disrupting agent configured for lysing cellular components to produce a reaction mixture comprising the cellular disrupting agent, biomolecular lysates and the starting fucan compositions; and
    removing the cellular disrupting agent and biomolecular lysates from the reaction mixture.

Providing the starting fucan compositions can comprise providing the starting fucan compositions as a solution, and the methods further can comprise collecting the compositions comprising the purified/modified fucans as a solid or in a reduced-impurities solution. The cellular disrupting agent can comprise a detergent, which can be an anionic detergent, a cationic detergent, or a non-ionic detergent. The detergent can comprise at least one of sodium dodecyl sulfate (SDS), benzalkonium chloride, Triton X 100®, Triton X 114®, Brij® detergents, Tween® detergents, sodium deoxycholate, and alkylbenzenesulfonates. Removing the cellular disrupting agent and biomolecular lysates can comprise adding to the reaction mixture a flocculant configured for flocculating the cellular disrupting agent and biomolecular lysates. Removing the cellular disrupting agent can comprise adding to the reaction mixture a precipitant configured for rendering the cellular disrupting agent insoluble in the reaction mixture, producing precipitates. Removing the biomolecular lysates can comprise adding to the reaction mixture a precipitant configured for rendering the biomolecular lysates insoluble in the reaction mixture, producing precipitates. The methods further can comprise adding to the reaction mixture a flocculant configured for flocculating the precipitates. The flocculant can comprise at least one of potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminoethyl acrylate methyl chloride; N,N-dimethylaminoethyl methacrylate methyl chloride quaternary; and polydiallyldimethyl-ammonium chloride.

Removing the anionic detergent can comprise anionic adsorption; removing the cationic detergent can comprise cationic adsorption; removing the non-ionic detergent can comprise micellar phase separation; and, removing the detergent can comprise hydrophobic adsorption. Removing the detergent can comprise:
    diluting the reaction mixture until the concentration of the detergent can be below a predetermined concentration; and
    subjecting the reaction mixture comprising the detergent to diafiltration over a tangential flow filtration filter with a molecular weight cut-off above the largest molecular weight of the detergent.
The methods can also comprise adding a chelating agent to the reaction mixture after providing the starting fucan compositions and before removing the cellular disrupting agent. The chelating agent can comprise ethylenediaminetetraacetic acid (EDTA), 2,3-dimercapto-1-propanol, ethylene diamine, porphine and/or citric acid, and the methods further can comprise adding an oxidant-quenching agent to the reaction mixture before removing the cellular disrupting agent to quench oxidants in the reaction mixture, or adding a bacteriostatic agent to the reaction mixture after providing the starting fucan compositions and before removing the cellular disrupting agent. The bacteriostatic agent can comprise sodium sulfite, ethylenediaminetetraacetic acid (EDTA), benzalkonium chloride, ethanol, and/or thiourea. The impurities removed can comprise at least one of particulates, lipids, fatty acids, phlorotannins, laminarins, alginates, proteins, Maillard reaction products, fucoxanthin, chlorophyll, bacteria, cellular components and DNA.

Methods for removing impurities from starting fucan compositions to obtain the compositions comprising the purified/modified fucans can also comprise:

providing starting fucan compositions comprising impurities in an aqueous starting solution;

mixing the aqueous starting solution with an organic solvent to produce an aqueous-organic phase mixture; and separating the aqueous-organic phase mixture to obtain an aqueous portion and an organic portion.

The methods further can comprise collecting the aqueous portion comprising the purified/modified fucans. The organic solvent can comprise at least one organic solvent with a relative polarity less than 0.765, which can be at least one of ethanol, isopropanol, methanol, benzene, decamethylcyclo-pentasiloxane, ethyl acetate, hexane, heptanol, octanol, decanol, heptane, isobutyl acetate, anisole, isopropyl acetate, 1-butanol, butyl acetate, methylisobutylketone, pentane, 1-pentanol, ethyl ether, and propyl acetate. The impurities removed can comprise at least one of particulates, lipids, fatty acids, phlorotannins, laminarins, alginates, proteins, Maillard reaction products, fucoxanthin, chlorophyll, bacteria, cellular components and DNA.

Methods for modifying the cationic content of starting fucan compositions can comprise:

providing starting fucan compositions in a starting solution; and diafiltering the starting solution across a tangential flow filtration filter with a solution of a chelating agent across a tangential flow filtration filter to produce a retentate fucan compositions.

The chelating agent can comprise at least one of ethylenediamine-tetraacetic acid (EDTA), 2,3-dimercapto-1-propanol, ethylene diamine, porphine or citric acid. The retentate fucan compositions can comprise a cationic content consisting essentially of sodium and/or potassium.

Methods for removing impurities from starting fucan compositions to obtain purified/modified fucans can further comprise:

providing starting fucan compositions comprising impurities;

subjecting the starting fucan compositions to a suitable pressure above 70 bar and a suitable temperature above 30° C. in a supercritical extractor; and filling the supercritical extractor with a supercritical fluid to remove impurities into the supercritical fluid; and removing the supercritical fluid containing the extracted impurities after a predetermined amount of time.

The methods further can comprise collecting the purified/modified fucans remaining in the supercritical extractor; the pressure can be between about 70 bar and about 2000 bar, and the temperature can be between about 30° C. and about 300° C. The starting fucan compositions can be a liquid or a solid. The supercritical fluid can comprise at least one of carbon dioxide, ethanol, ethane, hydrochloric acid, hydrofluoric acid, sulfuric acid and nitric acid. The predetermined amount of time can be between about 5 minutes and 50 hours. The impurities removed can comprise at least one of particulates, lipids, fatty acids, phlorotannins, laminarins, alginates, proteins, Maillard reaction products, fucoxanthin, chlorophyll, bacteria, cellular components and DNA.

These and other aspects, features and embodiments are set forth within this application, including the following Detailed Description and attached drawings. Unless expressly stated otherwise, all embodiments, aspects, features, etc., can be mixed and matched, combined and permuted in any desired manner.

These and other aspects, features and embodiments are set forth within this application, including the following Detailed Description and attached drawings. Unless expressly stated otherwise, all embodiments, aspects, features, etc., can be mixed and matched, combined and permuted in any desired manner.

Figure 1:
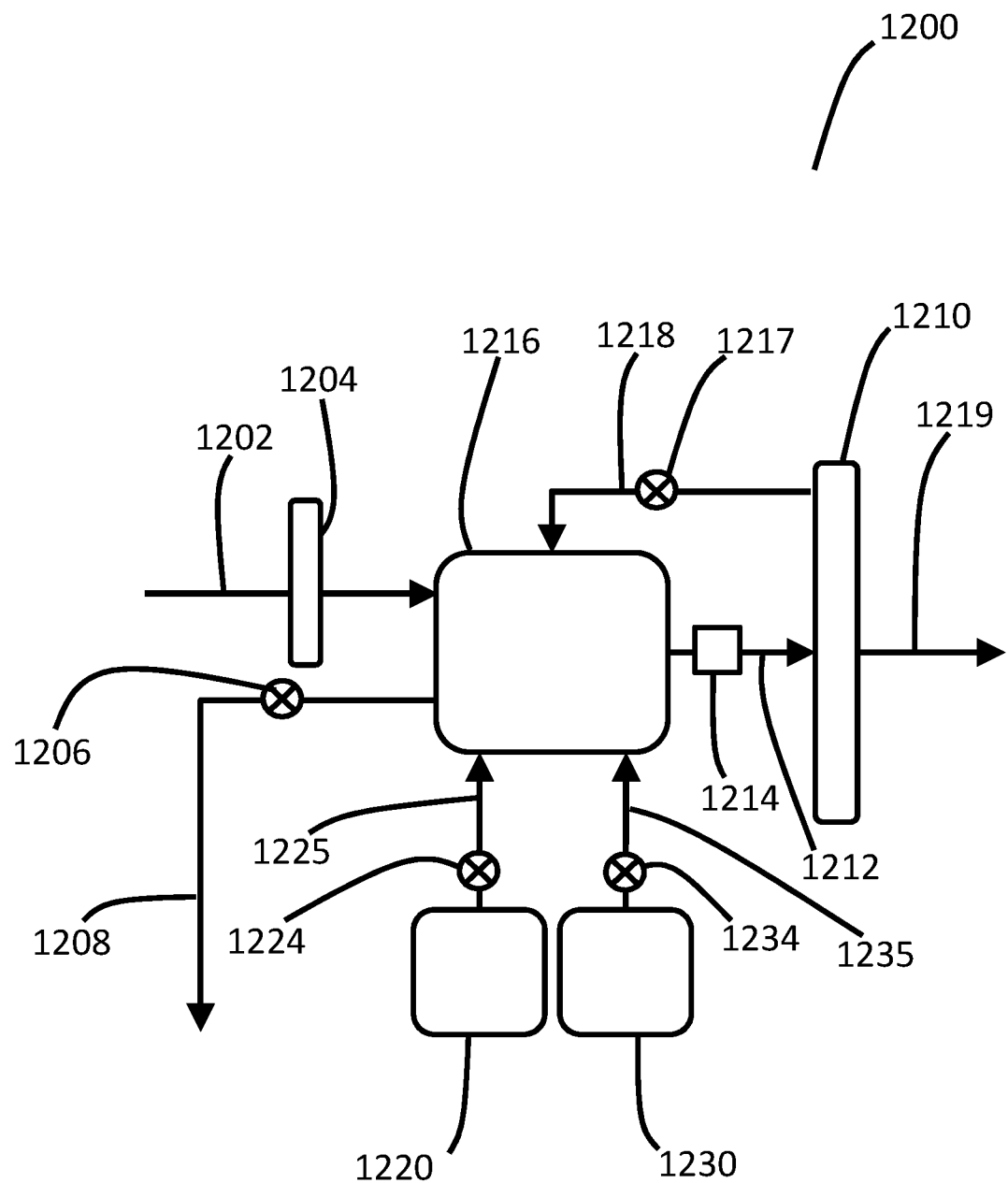
FIG. 1 schematically depicts an exemplary system for modifying the cationic content of a starting fucan composition and removing low molecular weight non-fucan components using a chelating agent in tangential flow filtration.

The drawings present exemplary embodiments of some aspects of the present compositions, methods, etc. Embodiments of the systems, methods, etc., herein may include further features or steps not shown in the drawings. Further, the exemplifications set out herein illustrate embodiments of the systems, methods, etc., in one or more forms, and such exemplifications are not to be construed as limiting the scope of the disclosure in any manner. The embodiments herein are not exhaustive and do not limit the disclosure to the precise form disclosed, for example in the following detailed description.

DETAILED DESCRIPTION

The current compositions, systems, methods, etc., presented herein comprise purified/modified fucans. The present compositions can be effective for medical treatments, post-surgical treatments, disease inhibition etc. In some embodiments, the fucan is fucoidan. The present purified/modified fucans can themselves be, or can be included on or in, medical devices, medical materials, combination products or in pharmaceutically acceptable, therapeutically and/or medically effective compositions.

The following paragraphs turn to a brief general discussion of some of the compositions herein comprising purified/modified fucans, including those that can be created using the methodologies discussed herein from starting fucan compositions via various methods that can be performed using any suitable reaction mixture such as solutions, suspensions, solids, gels or other modalities depending on the chosen method(s).

Compositions

The current compositions, systems, etc., presented herein provide, in certain embodiments, medically acceptable purified/modified fucan compositions comprising therapeutically effective amounts of purified/modified fucan compositions for the treatment of fibrous adhesions, such as surgical adhesions, as well as arthritis, psoriasis or other diseases as desired. The purified/modified fucans in the compositions can comprise more than about 75% w/w total fucose, galactose and sulfate, for example more than about 80% w/w and more than 84% w/w total fucose, galactose and sulfate. In some embodiments, the purified/modified fucans may further comprise up to at least about 5%, 7%, 9%, 10% or 11% w/w of at least one counterion. In some embodiments, the counterion is a pharmaceutically acceptable counterion. In some embodiments, the counterion is ionically bound to the sulfate group present on the fucan. Pharmaceutically acceptable counterions may include at least one of aluminum, arginine, benzathine, chloroprocaine, choline, sodium, potassium, lithium, ammonium, ethylene diamine, diethylamine, diethanolamine, ethanolamine, histidine, lysine, N-methyl glucamine, meglumine, procaine, triethylamine, zinc, calcium and magnesium. The sulfur containing component of fucan is bound via a C—O—S linkage. The oxygen in such linkage can be considered primarily bound to either the carbon or the sulfur depending on various factors. The term "sulfate" as used herein refers to both embodiments.

In certain embodiments, the purified/modified fucans herein comprise at least about 85% w/w, 90% w/w, 94% w/w, 97% w/w or 98% w/w fucose, galactose, sulfate, and counterions. Exemplary counterions include up to about 7%, 8%, 9%, 10%, 11%, 12%, 13%, 14%, or 15% w/w calcium, magnesium, potassium and/or sodium. In some embodiments, the purified/modified fucan comprises at least about 25%, 30% or 35% w/w fucose. In some embodiments, the purified/modified fucan comprises less than about 10%, 5% or 4% w/w galactose. In some embodiments, the purified/modified fucan consists essentially of, or consists of, such total of fucose, galactose, sulfate and counterion components. In some embodiments, the fucans herein substantially or completely lack all sugar components other than the fucose and galactose. In some embodiments, the fucans herein substantially or completely lack one or more of glucuronic acid, mannose, rhamnose, xylose, galactose, or glucose; as used in this sentence, "substantially lacks" indicates that the presence, if any, of such sugar components is low enough that the presence is pharmaceutically and medically immaterial.

In some further embodiments, the purified/modified fucans herein can be used for a plurality of applications, including the inhibition, prevention, removal, reduction, or other treatment of fibrous adhesions and other targets and other diseases and/or conditions. Treatment includes that the fucans reduce or prevent the development of a target disease or other condition, such as reducing or preventing the formation of fibrous adhesions at a target site, which is typically a selected target site identified by a surgeon or other practitioner as comprising or reasonably susceptible to having fibrous adhesions (or other diseases or conditions), and also includes elimination of existing diseases or other conditions, including for example the elimination of already-existing fibrous adhesions. For such inhibition, prevention, removal, reduction, or other treatment, the fucan is typically provided in a medically acceptable medical device, combination product, or pharmaceutically effective composition that contains additional components such as binders, adjuvants, excipients, etc., as well as, if desired, additional medically active substances such as secondary drugs that are contained within the composition but not attached to the fucan, and/or that can be attached to the fucan.

In still further embodiments, the compositions comprising the purified/modified fucans herein can be solids, for example solid compositions comprising a water content of less than about 7% w/w, for example less than about 6%, 5% w/w, 4% w/w, 3% w/w or 2% w/w water content.

The molecular weight distribution of the purified/modified fucans may be measured using any desired, appropriate measurement system. Different systems can yield different readings or results from different compositions having essentially the same make-up, or even from the same batch when measured differently. One suitable measurement system is an aqueous gel permeation chromatography set up consisting essentially of one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C., a refractive index detector at about 30° C., 0.1M sodium nitrate mobile phase run at 0.6 mL/min, and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa. The peak molecular weight standard curve may further comprise a dextran standard with a peak molecular weight between 3 kDa and 5 kDa.

The purified/modified fucans herein can have a molecular weight distribution wherein at least about 25%, 30%, 40%, 50%, 60%, 70%, 75%, 90%, 92%, 97% or 98% w/w of the distribution is greater than 100 kDa. The purified/modified fucans herein may comprise fucans with a molecular weight distribution wherein at least about 50%, 60%, 70%, 80%, or 90% w/w of the distribution is greater than 200 kDa. The purified/modified fucans herein can have a molecular weight distribution wherein at least about 25%, 30%, 40%, 50%, 60%, 70%, or 75% w/w of the distribution is greater than 500 kDa. The purified/modified fucans herein can have a molecular weight distribution wherein at least about 5%, 10%, 20%, 30%, or 40% w/w of the distribution is greater than 1600 kDa.

The purified/modified fucans herein can have a weight average molecular weight greater than about 100 kDa, for example between about 100 kDa and about 10,000 kDa, between about 200 kDa and about 8,000 kDa, between about 350 kDa and about 8,000 kDa, between about 450 kDa and about 8,000 kDa, between about 580 kDa and about 8,000 kDa, or between about 800 kDa and about 2,000 kDa. The purified/modified fucans herein can have a peak molecular weight greater than about 70 kDa, for example between about 70 kDa and about 1200 kDa, between about 100 kDa and about 1200 kDa, between about 200 kDa and about 1200 kDa, between about 400 kDa and about 1200 kDa, or between about 400 kDa and about 900 kDa.

The purified/modified fucans herein can have a number average molecular weight greater than about 50 kDa, between about 50 kDa and about 1,000 kDa, between about 70 kDa and about 1000 kDa, between about 150 kDa and about 1000 kDa, between about 250 kDa and about 1000 kDa, or between about 250 kDa and about 700 kDa.

The purified/modified fucans herein can have a sulfation level of between about 10% w/w and 70% w/w, between about 20% w/w and 65% w/w, between about 30% w/w and 60% w/w, or between about 40% w/w and 60% w/w.

The purified/modified fucans herein can have a molar ratio of total fucose:total sulfate of between about 1:0.5 and 1:4, between about 1:0.8 and 1:3.5, between about 1:1 and 1:2.5, between about 1:1.2 and 1:2.0, or between about 1:1.5 and 1:3. Purified/modified fucans herein can have a molar ratio of total fucose plus galactose:total sulfate of between about 1:0.5 and 1:4, between about 1:0.8 and 1:3.5, between about 1:1 and 1:2.5, between about 1:1.2 and 1:2.0, or between about 1:1.5 and 1:3.

The purified/modified fucans herein can have a total carbohydrate content of between about 27% w/w and 70% w/w, between about 30% w/w and 80% w/w, between about 40% w/w and 90% w/w, or between about 50% w/w and 96% w/w. The purified/modified fucans herein can have a fucose content as a percentage of total carbohydrate of about 30% w/w and 100% w/w, between about 40% w/w and 95% w/w, or between about 50% w/w and 90% w/w. The fucans herein may have a galactose content as a percentage of total carbohydrate of 0% w/w and 60% w/w, between about 5% w/w and 30% w/w, or between about 8% w/w and 10% w/w. The fucans herein may have a glucuronic acid content as a percentage of total carbohydrate content between about 0% w/w and 10% w/w, a mannose content as a percentage of total carbohydrate content between about 0% w/w and 7% w/w, a rhamnose content as a percentage of total carbohydrate content between 0% w/w and 4% w/w, and a xylose content as a percentage of total carbohydrate content between 0% w/w and 20% w/w. The fucans herein may have a total glucuronic acid, mannose, rhamnose, glucose and xylose content of less than about 30% w/w, or less than about 12% w/w.

In some embodiments, the purified/modified fucans herein, when dissolved at a concentration of 50 mg/mL in water, have a viscosity of between about 4 cP and about 50 cP, between about 5 cP and about 40 cP, between about 10 cP and about 30 cP, about 15 cP, about 20 cP and about 25 cP. In certain embodiments, the purified/modified fucans herein, when dissolved in water at 1 mg/mL through 100 mg/mL form a solution that is one of clear and colorless, clear and light yellow or clear and light brown.

The purified/modified fucans herein can be provided in a paste, gel, patch, film, spray, liquid, lotion, cream, solution, suspension, solid, implant, microsphere or other desired form.

The compositions presented herein can be a solid consisting essentially of the purified/modified fucans. The purified/modified fucan may consist essentially of fucose, galactose, sulfate and counterions.

The purified/modified fucans herein can be in a solution comprising between about 0.01 mg/mL and about 300 mg/mL of fucan, for example between about 0.1 mg/mL and about 100 mg/mL, between about 1 mg/mL and about 50 mg/mL and between about 20 mg/mL and about 80 mg/mL. The fucan may consist essentially of fucose, galactose, sulfate and counterions.

The purified/modified fucans can be in a gel comprising between about 100 mg/mL and about 1000 mg/mL of fucan, for example between about 100 mg/mL and about 500 mg/mL and between about 300 mg/mL and about 800 mg/mL. The fucan may consist essentially of fucose, galactose, sulfate and counterions.

The purified/modified fucans can be in a film comprising between about 100 mg/mL and about 1000 mg/mL of fucan, for example between about 100 mg/mL and about 500 mg/mL and between about 300 mg/mL and about 800 mg/mL. The fucan may consist essentially of fucose, galactose, sulfate and counterions.

The purified/modified fucans herein can be administered as a component of a medical device, combination product and/or pharmaceutical composition comprising any number of pharmaceutically acceptable excipients, for example, gelatin, hypromellose, lactose, water for injection USP, sodium chloride, sodium phosphate, sodium citrate, sodium ascorbate, phosphate buffers, citrate buffers, phosphate-citrate buffers, pluronic, cellulose, alginate, acrylate, hyaluronic acid, polyethylene glycol, chitosan, injectable excipient and lactated Ringer's injection USP.

The purified/modified fucans herein can be administered as a paste, gel, patch, film, spray, liquid, lotion, cream, solution, suspension, solid, implant, microsphere or other desired form.

The purified/modified fucans can be administered via intravenous, intraarticular, intralesional, intravaginal, rectal, intramuscular, intraperitoneal, subcutaneous, topical, intranasal, intraocular or oral administration routes. The purified/modified fucans can be directly delivered to the disease site. The purified/modified fucans can be continuously released to the disease site via controlled release from a polymeric dosage form.

The purified/modified fucans herein can be administered as a component of a pharmaceutical composition comprising the purified/modified fucans and at least one other drug. The drug can be at least one of paclitaxel, doxorubicin, camptothecin, etoposide, mitoxantrone, methotrexate, menadione, plumbagin, juglone, beta-laperchone cyclosporin, sulfasalazine, steroid, rapamycin, retinoid, docetaxel, colchicine, antisense oligonucleotide and ribozyme.

In certain embodiments, the purified/modified fucans herein can have an acetyl content of less than about 5% w/w, less than about 2% w/w, and about 0% w/w. In some embodiments, the purified/modified fucans herein comprise substantially 0% w/w acetyl content when measured by 2D $^1H$-$^{13}C$ heteronuclear multiple quantum coherence at 70° C. with solvent signal suppression on a 600 MHz spectrometer equipped with 5-mm cold probe, in the range from 10-30 ppm in the carbon dimension, in 8 increments of 256-512 scans each.

Methods

Methods, systems, etc., are provided for purifying and/or modifying a fucan, for example from a starting fucan composition comprising fucans, for example a feedstock fucan composition, or other fucan-containing compositions. "Impurities" as used herein refers to any component of the fucan that is not fucose, galactose, sulfate or a counterion, and to any non-fucan component or compound or substance present in a composition comprising a fucan. Impurities can be bound to the fucan, for example, proteins ionically and/or chemically bound to the fucan, sugar residues other than fucose and galactose that are part of the fucan polymeric structure, other saccharides chemically bound to the fucan, and non-fucan impurities that are not bound to the fucan but are present in a starting fucan composition such as a feedstock fucan composition. Examples of such impurities include but are not limited to particulates, lipids, fatty acids, phlorotannins, laminarins, alginates, proteins, Maillard reaction products, fucoxanthin, chlorophyll, bacteria, cellular components and DNA, several of which contain chromophores and result in the presence of brown, yellow and green colors in starting fucan compositions and several of which can be ionically and/or chemically bound to or part of the fucan in the starting fucan composition. In certain embodiments, the methods, etc., herein can be used to prepare purified/modified fucans comprising at least about 88% w/w, 89% w/w, 90% w/w, 91% w/w, 92% w/w, 93% w/w, 94% w/w, 95% w/w, 96% w/w, 97% w/w, 97.1% w/w, 98% w/w, 98.8% w/w, 99% w/w, 99.5% w/w, or 99.9% w/w of fucose, galactose, sulfate and counterions. In some embodiments, the purified/modified fucan comprises at least about 75%, 78%, 80%, 82% or 84% w/w fucose, galactose and sulfate. In some embodiments, the purified/modified fucan comprises less than about 0.1%, 0.5%, 1%, 2.9%, 3%, 4%, 5%, 6%, 7%, 8%, 9%, 10%, 11%, or 12% w/w impurities. Some of these impurities may cause dangerous complications upon the medical and/or surgical use of fucans.

In some embodiments, the current disclosure presents purified/modified fucans with low levels of impurities that are suitable for medical and surgical applications, for example, the prevention of fibrous adhesions.

The following paragraphs turn to a brief general discussion of some of the methodologies that can be used to create the purified/modified fucans herein.

Physically Induced Flocculation

A starting fucan composition, such as a feedstock fucan composition, comprising high levels of impurities undergoes a flocculation of impurities, which can be a physically-induced flocculation. The method can comprise: providing a starting fucan composition; adding a flocculation aid to the starting fucan composition to produce a reaction mixture; flocculating the impurities in the starting fucan composition by heating the reaction mixture; separating the flocculated impurities from the reaction mixture; and collecting the desired purified/modified fucan after the separating.

Flocculating the impurities by heating the reaction mixture may comprise heating the reaction mixture while subjecting the reaction mixture to a pressure in excess of atmospheric pressure. Suitable flocculation aids include without limitation, salts and/or bases, for example chlorides, bromides, iodides, fluorides, sulfates, sulfites, carbonates, bicarbonates, phosphates, nitrates, nitrites, acetates, citrates, silicates, oxides, hydroxides and/or cyanides of an alkali metal, alkaline earth metal, aluminum and/or ammonium, for example, sodium chloride, sodium sulfate, potassium chloride, calcium sulfate, sodium phosphate, sodium nitrate, lithium chloride, lithium nitrate, ammonium chloride, sodium carbonate, sodium hydroxide. Separating the flocculated impurities from the reaction mixture may comprise one or more of centrifuging, filtering, sedimentation or hydrodynamic flow separation of the reaction mixture.

The methods, etc., herein may further comprise desalting the starting fucan composition before adding a flocculation aid. The desalting may comprise diafiltrating the starting fucan composition as a solution in water across a molecular weight cutoff (MWCO) tangential flow filtration (TFF) filter. The diafiltrating may comprise diafiltrating the starting fucan composition with distilled water. The molecular weight cutoff TFF filter can have a molecular weight cutoff smaller than a desired molecular weight separation point or target in or for the purified/modified fucan, for example a 50 kDa, 70 kDa, 100 kDa, 200 kDa, 300 kDa, 500 kDa or 1000 kDa molecular weight cut-off.

The method can be performed in basic and neutral environments. The adding of a flocculation aid to the starting fucan composition may therefore comprise rendering the starting fucan composition basic to prevent or inhibit the fucan in the starting fucan composition from degrading, because fucans are prone to degradation in acidic environments. In other embodiments, the method can be carried out by maintaining the reaction mixture at or near a pH of 7 or more.

In some embodiments, the starting fucan composition may be provided as a solution. Example fucans suitable for treatment by the above method include without limitation fucoidan, and the concentration of the fucan in solution can be between 0.01% w/v and 50% w/v. Impurities that can be removed by the above method include without limitation particulates, lipids, fatty acids, phlorotannins, laminarins, alginates, proteins, Maillard reaction products, fucoxanthin, chlorophyll, bacteria, cellular components and DNA.

Solid Phase Extraction

Fucans in a starting fucan composition such as a feedstock fucan composition containing undesirable levels of impurities, including very high levels of impurities such as in a raw feedstock composition, is subjected to a solid phase extraction. The methods can comprise: providing in solid form a starting fucan composition comprising impurities and an extraction media incapable of dissolving fucans, configured for dissolving the impurities; mixing the starting fucan composition with the extraction media to form a mixture of an undissolved solid fucan composition and an extraction media, the extraction media containing dissolved impurities; separating the purified undissolved solid state fucan from the extraction media containing dissolved impurities; and collecting the purified/modified fucan as a solid after removing the purified/modified fucan from the extraction media. The separating may comprise one or more of, for example, centrifugation, filtration, sedimentation and hydrodynamic fluid separation.

The extraction media can comprise, for example, one or more of a base, a detergent and an oxidizing agent. Suitable extraction media that do not dissolve the fucan include organic solvents with a relative polarity less than 0.765, for example, ethanol, isopropanol, methanol, benzene, diethyl ether, decamethylcyclo-pentasiloxane, ethyl acetate, butanol, hexane, heptane, heptanol, octanol and decanol. Suitable bases include without limitation sodium hydroxide, potassium hydroxide, lithium hydroxide, and calcium hydroxide. Suitable oxidizing agents include without limitation one or more of hydrogen peroxide, urea peroxide, and oxidizing bleaches, including sodium hypochlorite. Suitable detergents include without limitation nonionic surfactants, for example the Tween®, Brij® and Triton® ranges of detergents; anionic surfactants, for example sodium dodecyl sulfate (SDS), sodium deoxycholate; and cationic surfactants, for example benzalkomium chloride (BAC). Particular fucans lending themselves to the methods herein include, but are not limited to fucoidan. The mixing of the original, e.g., starting, fucan composition with the extraction media may extend from one minute to 120 hours.

The methods may further comprise desalting the starting fucan composition before providing in solid form the starting fucan composition. The desalting may comprise diafiltrating the starting fucan composition as a solution in water across a molecular weight cutoff (MWCO) tangential flow filtration (TFF) filter. The diafiltrating may comprise diafiltrating the starting fucan composition with distilled water. The molecular weight cutoff TFF filter can have a molecular weight cutoff smaller than a desired molecular weight separation point or target in or for the purified/modified fucan, for example a 50 kDa, 70 kDa, 100 kDa, 200 kDa, 300 kDa, 500 kDa or 1000 kDa molecular weight cut-off. The diafiltrating may further comprise pre-filtering the starting fucan composition in through a suitable pre-filter to remove particulate matter. The method may further comprise lyophilizing a suitable starting fucan composition in solution prior to providing in solid form the starting fucan composition. The method may further comprise precipitating from a solution a suitable starting fucan composition prior to providing in solid form the starting fucan composition. Suitable precipitants include without limitation ethanol, isopropanol, propanol, acetone, methanol, dimethyl sulfoxide, dimethyl formamide, ethylene glycol, tetrahydrofuran, acetonitrile, glyme, diglyme, dioxane, the solubility of the fucan decreasing as the polarity of the precipitating fluid decreases. Impurities that can be removed by the above method include without limitation particulates, lipids, fatty acids, phlorotannins, laminarins, alginates, proteins, Maillard reaction products, fucoxanthin, chlorophyll, bacteria, cellular components and DNA.

Chemically Induced Precipitation

A starting fucan composition, such as a feedstock fucan composition, containing high levels of impurities including for example, suspended particulates, undergoes a chemically-induced precipitation of impurities. In certain embodiments, the methods can comprise: providing a starting fucan composition in a starting solution; precipitating the impurities from the starting solution by means of an ionic-multivalent impurity precipitant to provide a mixture of suspended impurities, precipitated impurities and supernatant; separating the suspended impurities and precipitated impurities from the supernatant solution; and collecting the supernatant solution comprising the desired purified/modified fucan after separating the suspended impurities and precipitated impurities from the supernatant.

Suitable impurity precipitants include ionic-multivalent salts and/or bases of divalent and trivalent cations. Examples of such suitable salts include without limitation chlorides, bromides, iodides, fluorides, sulfates, sulfites, carbonates, bicarbonates, phosphates, nitrates, nitrites, acetates, citrates, silicates and/or cyanides of alkaline earth metals, zinc, aluminum, copper and iron. Examples of such suitable bases include without limitation hydroxides and/or oxides of alkaline earth metals, zinc, aluminum, copper and/or iron. Separating the suspended impurities and precipitated impurities from the supernatant solution may comprise flocculating the impurities in the mixture. Suitable flocculants include without limitation potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminoethyl acrylate methyl chloride; N,N-dimethylaminoethyl methacrylate methyl chloride quaternary; and polydiallyldimethyl-ammonium chloride. As can be seen from the foregoing list of flocculants, in some embodiments, the flocculant can be the impurity precipitant. Separating the precipitated, suspended and/or flocculated impurities from the supernatant solution may comprise at least one of centrifuging, filtering, sedimentation and hydrodynamic flow separation of the mixture of impurities and the supernatant solution.

The methods may further comprise desalting the starting fucan composition before providing the starting fucan composition. The desalting may comprise diafiltrating the starting fucan composition as an aqueous solution across a TFF filter. The diafiltrating may comprise diafiltrating the starting fucan composition with distilled water. The diafiltrating may comprise diafiltrating the starting fucan composition across a TFF filter with a MWCO of 5 kDa, 10 kDa, 30 kDa, 50 kDa, 70 kDa or 100 kDa. The diafiltrating may further comprise pre-filtering the starting fucan composition in through a suitable pre-filter to remove particulate matter.

The methods may further comprise maintaining a pH of between about 7 and 14 to inhibit or prevent degradation of fucans in acidic environments. Maintaining the pH between about 7 and 14 may comprise the addition of a suitable base, for example, sodium hydroxide. A suitable base may be added to the starting fucan composition before precipitating impurities from the solution by means of an ionic-multivalent impurity precipitant. In other embodiments, a suitable base may be added to the mixture of precipitated impurities and supernatant solution after precipitating impurities from the solution by means of an ionic-multivalent impurity precipitant. In yet other embodiments, a suitable base may be added to the supernatant solution after separating the suspended impurities and precipitated impurities from the supernatant solution.

Example fucans suitable for treatment by the above method include without limitation fucoidan, and the concentration of the fucan in solution can be between 0.01% w/v and 50% w/v. Impurities that can be removed by the above method include without limitation particulates, lipids, fatty acids, phlorotannins, laminarins, alginates, proteins, Maillard reaction products, fucoxanthin, chlorophyll, bacteria, cellular components and DNA.

Lysis and Flocculation

A starting fucan composition, such as a feedstock fucan composition, containing high levels of impurities undergoes lysis and flocculation. The methods in this example can comprise: providing a starting fucan composition; rendering the starting fucan composition alkaline; adding to the starting fucan composition a cellular disrupting agent to produce a reaction mixture, the cellular disrupting agent lysing cellular components in the starting fucan composition and releasing into the alkaline reaction mixture lysates comprising biomolecular components; removing from the reaction mixture the cellular disrupting agent and at least a portion of the impurities to leave undegraded the desired purified fucan.

The removing of the cellular disrupting agent may comprise any one or more of precipitation, flocculation, tangential flow filtration, micellar phase separation, ionic adsorption, and hydrophobic adsorption. The removal of impurities may comprise any one or more of precipitation, flocculation, tangential flow filtration, micellar phase separation, ionic adsorption, and hydrophobic adsorption. Any of these removal methods or combinations of removal methods may comprise centrifuging, filtering, sedimentation or hydrodynamic flow separation of any mixture of solid and liquid phases.

Suitable cellular disrupting agents include without limitation anionic, non-ionic and cationic detergents, for example sodium dodecyl sulfate (SDS), benzalkonium chloride, Triton X 100®, Triton X 114®, Brij® detergents, Tween® detergents, sodium deoxycholate, and alkylbenzenesulfonates.

In one embodiment of the methods, the cellular disrupting agent is sodium dodecyl sulfate (SDS) and the removing of the cellular disrupting agent comprises adding a precipitant for rendering the cellular disrupting agent insoluble in the alkaline reaction mixture and to thereby precipitate the cellular disrupting agent. In this embodiment, the removing of the cellular disrupting agent may further comprise adding a flocculant to the reaction mixture to flocculate the precipitated cellular disrupting agent and along with it at least a portion of the impurities. The removing of the cellular disrupting agent may further comprise centrifuging after the flocculation.

Suitable precipitants for sodium dodecyl sulfate and alkylbenzenesulfonates include without limitation potassium hydroxide, potassium chloride, calcium chloride, calcium carbonate and barium chloride. Suitable flocculants include without limitation potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminoethyl acrylate methyl chloride; N,N-dimethylaminoethyl methacrylate methyl chloride quaternary; and polydiallyldimethyl-ammonium chloride.

It is to be understood hereby that the cellular disrupting agent may undergo a change in the process of precipitation. For example without limitation, if the cellular disrupting agent is sodium dodecyl sulfate (SDS), the precipitant may be potassium hydroxide (KOH) and the sodium cation may be replaced as part of the precipitation process by potassium, the resulting potassium dodecyl sulfate being insoluble in the reaction mixture and thereby precipitating. The dodecyl sulfate cation, which functionally is the cellular disrupting portion of the SDS, stays intact in this process.

In yet other embodiments of the methods, the cellular disrupting agent may be one or more of sodium dodecyl sulfate (SDS) and sodium deoxycholate and the removing of the cellular disrupting agent comprises anionic adsorption. The anionic adsorption may comprise adding a suitable positively charged adsorbent for a suitable amount of time, followed by the removal of the adsorbent. The anionic adsorption may further comprise flowing the reaction mixture over a column or filter packed with a suitable positively charged adsorbent at a suitable flow rate.

In yet other embodiments of the methods, the cellular disrupting agent may be benzalkonium chloride and the removing of the cellular disrupting agent comprises cationic adsorption. The cationic adsorption may comprise adding a suitable negatively charged adsorbent for a suitable amount of time, followed by the removal of the adsorbent. The cationic adsorption may further comprise flowing the reaction mixture over a column or filter packed with a suitable negatively charged adsorbent at a suitable flow rate.

In yet other embodiments of the methods, the cellular disrupting agent may be one or more of Triton X 100®, Triton X 114®, Brij® and Tween® detergents and the removing of the cellular disrupting agent comprises micellar phase separation. The micellar phase separation may comprise altering the temperature of the reaction mixture such that the temperature of the reaction mixture exceeds the cloud point of the cellular disrupting agent. The micellar phase separation may comprise centrifuging the reaction mixture to obtain the desired phase separation.

In further embodiments of methods, the cellular disrupting agent may be any one or more of sodium dodecyl sulfate (SDS), benzalkonium chloride, Triton X 100®, Triton X 114®, Brij® detergents, Tween® detergents, sodium deoxycholate, and alkylbenzenesulfonates, and the and the removing of the cellular disrupting agent comprises one or more of hydrophobic adsorption and a combination of dilution and tangential flow filtration (TFF). The hydrophobic adsorption may comprise adding a suitable hydrophobic adsorbent for a suitable amount of time, followed by the removal of the adsorbent. The hydrophobic adsorption may comprise flowing the reaction mixture over a column or filter packed with a suitable hydrophobic adsorbent at a suitable flow rate. The removal by dilution and TFF may comprise diluting the reaction mixture such that the cellular disrupting agent falls below its critical micellar concentration and thus can be removed by means of tangential flow filtration over a suitable molecular weight cut-off (MWCO) TFF filter that allows for the permeation of the cellular disrupting agent from a fucan containing retentate. The removal by dilution and TFF may involve diafiltering the reaction mixture over the TFF filter with a suitable number of diavolumes.

The methods may further comprise adding a chelating agent to the reaction mixture to chelate free multivalent cations in the reaction mixture. The chelating agent may be added after providing the starting fucan composition and before the removing of the cellular disrupting agent. The methods may further comprise quenching oxidants in the reaction mixture. The quenching of oxidants may comprise adding an oxidant-quenching agent to the reaction mixture before or after the removing of the cellular disrupting agent.

The methods may comprise adding a bacteriostatic agent to the reaction mixture. The bacteriostatic agent may be added after providing the starting fucan composition and before the removing of the cellular disrupting agent. Suitable bacteriostatic agents include without limitation sodium sulfite, ethylenediaminetetraacetic acid (EDTA), benzalkonium chloride, ethanol, and thiourea.

Suitable chelating agents include without limitation ethylenediaminetetraacetic acid (EDTA), 2,3-dimercapto-1-propanol, ethylene diamine, porphine and citric acid. Suitable oxidant-quenching agents include without limitation sulfite, nitrite and phosphite salts. As is evident from the above, several of the compounds listed may have more than one function in the methods.

Suitable hydrophobic adsorbents include without limitation activated carbon, diatomaceous earth, acrylic ester non-ionic resins, polystyrene non-ionic resins, styrene-divinylbenzene (DVB) non-ionic resins. Suitable anionic adsorbents include without limitation: amine functionalized styrene-DVB resins, amine functionalized methacrylate resins, amine functionalized methyl methacrylate resins, amine functionalized butyl methacrylate resins, amine functionalized agarose resins, amine functionalized dextran resins, amine functionalized ceramic based resins, amine functionalized silicates, and lipid removal agent (LRA).

In some embodiments, the starting fucan composition may be provided as a solution. Example fucans suitable for treatment by the above method include without limitation fucoidan. The starting fucan composition may have a fucan concentration in solution of greater than 0.1% w/v and less than 30% w/v. The cellular disrupting agent may have a concentration in solution of greater than 0.1% w/v and less than 60% w/v. Impurities that may be removed by the above method include without limitation particulates, lipids, fatty acids, phlorotannins, laminarins, alginates, proteins, Maillard reaction products, fucoxanthin, chlorophyll, bacteria, cellular components and DNA.

Liquid-Liquid Extraction

Fucans in a starting fucan composition such as a feedstock fucan composition containing undesirable levels of impurities undergoes liquid-liquid extraction. The methods can comprise: providing the starting fucan composition in an aqueous starting solution; mixing the starting solution with an organic solvent to obtain an aqueous-organic phase mixture having an aqueous portion comprising a purified/modified fucan, and an organic portion comprising hydrophobic impurities; separating the aqueous portion from the organic portion; and collecting the aqueous portion comprising the purified/modified fucan.

The methods may further comprise desalting the starting fucan composition before mixing with the aqueous starting solution an organic solvent. The desalting may comprise diafiltrating the starting fucan composition as a solution in water across a molecular weight cutoff (MWCO) tangential flow filtration (TFF) filter. The diafiltrating may comprise diafiltrating the starting fucan composition with distilled water. The molecular weight cutoff TFF filter can have a molecular weight cutoff smaller than a desired molecular weight separation point or target in or for the purified/modified fucan, for example a 5 kDa, 10 kDa, 30 kDa, 50 kDa, 70 kDa, 100 kDa, 200 kDa, 300 kDa, 500 kDa or 1000 kDa molecular weight cut-off. The diafiltrating may further comprise pre-filtering the starting fucan composition in through a suitable pre-filter to remove particulate matter.

Mixing the aqueous starting solution with an organic solvent may comprise shaking the aqueous-organic solvent mix, stirring the aqueous-organic solvent mix, exposing the aqueous-organic solvent mix to high-shear, recirculating the aqueous phase into the organic phase and recirculating the organic phase into the aqueous phase.

Separating the aqueous portion from the organic portion may comprise at least one of least one of centrifugation, decanting, separatory funnel separation and hydrodynamic flow separation.

Suitable organic solvents for use with this method include organic solvents with a relative polarity less than 0.765, for example, heptane, isobutyl acetate, anisole, isopropyl acetate, 1-butanol, butyl acetate, methylisobutylketone, pentane, 1-pentanol, ethyl acetate, ethyl ether, and propyl acetate. The organic phase may contain impurities, for example without limitation, lipids, fatty acids, phlorotannin, proteins, fucoxanthin and/or chlorophyll.

Diafiltration

Fucans in a starting fucan composition such as a feedstock fucan composition containing undesirable levels of impurities undergoes diafiltration. The methods can comprise: subjecting the starting fucan composition in a starting solution to diafiltration with a chelating agent solution across a first tangential flow filtration filter to produce a first retentate fucan composition and a permeate solution of chelated cationic components; and subjecting the first retentate fucan composition to diafiltration with a secondary diafiltration solution across a second tangential flow filtration filter to separate residual chelating agent from the first retentate fucan composition, producing a second retentate fucan composition comprising the desired purified/modified fucan. Subjecting the first retentate fucan composition to diafiltration across a second tangential flow filtration filter may comprise subjecting the first retentate fucan composition to diafiltration across the first flow filtration filter. That is, the same filter can be employed in both diafiltration processes.

Subjecting the starting fucan composition to diafiltration may comprise pre-filtering the starting fucan composition through a pre-filter to remove undesired particulate material. Subjecting the starting fucan composition to diafiltration with a chelating agent may comprise subjecting the starting fucan composition to diafiltration with one of ethylenediamine-tetraacetic acid (EDTA), 2,3-dimercapto-1-propanol, ethylene diamine, porphine or citric acid.

The starting fucan composition may have a fucan concentration in solution of greater than 0.1% w/v and less than 30% w/v. The chelating agent may have a concentration in solution of greater than 0.1% w/v and less than 60% w/v.

The resulting first and/or second retentate compositions can comprise a cationic content consisting essentially of sodium and/or potassium.

FIG. 1 shows a schematic diagram of a cationic content modification system 1200 for obtaining a modification of the cationic content and/or level of a starting fucan composition. A starting fucan composition in solution is supplied via input supply line 1202 to fucan container 1216. The starting fucoidan in a suitable solvent can be pre-filtered through pre-filter 1204 to remove any undesired particulate matter. The gauge of the pre-filter will typically be greater than the largest polymer molecules to be separated by means of the cationic content modification system 1200.

TFF input pump 1214 pumps starting fucan composition to TFF filter 1210 via TFF supply line 1212. TFF filter 1210 is typically supplied as a cassette designed to allow an input fluid supplied to it to pass over its filter on its retentate side, while allowing a permeate to exit via one output line and treated input fluid to leave as retentate via another output line. TFF input pump 1214 provides a level of pressure over TFF filter 1210 between its retentate and permeate sides. In FIG. 1, the retentate of TFF filter 1210 is returned to fucan container 1216 via TFF retentate return line 1218 and TFF retentate valve 1217, while permeate is produced via TFF permeate output line 1219 for use outside cationic content modification system 1200 or to be discarded.

While TFF input pump 1214 recirculates the prefiltered fucoidan and retentate over TFF filter 1210, a chelating agent, for example without limitation one of ethylenediamine-tetraacetic acid (EDTA), 2,3-dimercapto-1-propanol, ethylene diamine, porphine or citric acid, can be added to the starting fucan composition in fucan container 1216 from first diafiltration solution container 1220 via first diafiltration solution supply line 1225. The chelating agent is used both to replenish solvent lost via the permeate on TFF permeate output line 1219 and/or to ensure that a predetermined number of diavolumes of input fucan and chelating agent are circulated over the TFF filter 1210. The chelating agent sequesters the cations in the starting fucan composition, in particular multivalent cations, as chelates which then pass through the TFF filter 1210 into the permeate. By controlling first diafiltration solution valve 1224, the chelating agent can be added in a pulse process. In other embodiments, the chelating agent can be added in a continuous mode. The number of diavolumes of chelating agent to process over TFF filter 1210 can be predetermined. The process can be continued for a predetermined period of time, for example between about 1 and about 6 hours, between about 3 and about 12 hours and between about 10 and about 24 hours. The process can be continued for a predetermined number of diavolumes of the chelating agent, for example between about 1 and about 4 diavolumes, between about 3 and about 6 diavolumes, between about 5 and about 10 diavolumes and between about 7 and about 20 diavolumes. The process can be continued and the cationic content in the fucan container 1216 can be measured and the TFF process terminated when a desired cationic content has been attained, for example a cationic content comprising of below 10 parts per million (ppm), below 1 ppm, below 0.1 ppm and below 0.01 ppm of multivalent cations. The diafiltration of the starting fucan composition in solution across TFF filter 1210 with the first diafiltration solution affords a first retentate fucan composition with a modified cationic content.

The next step in the process is to remove remaining chelating agent from the first retentate fucan composition in fucan container 1216. This can be done by shutting first diafiltration solution valve 1224, cationic content modification system output valve 1206, and allowing a secondary diafiltration solution from second diafiltration solution container 1230 to enter fucan container 1216 via second diafiltration solution supply line 1235 and second diafiltration solution valve 1234. The mix in fucan container 1216 is then subjected to TFF across TFF filter 1210 as before via TFF supply line 1212, TFF input pump 1214, TFF retentate return line 1218, and TFF retentate valve 1217. The secondary diafiltration solution may comprise for example without limitation any one or more of deionized water, a solution of a bacteriostatic agent, and a salt. The bacteriostatic agent can be, for example without limitation, sodium sulfite, EDTA, benzalkonium chloride, ethanol, thiourea. Suitable salts include without limitation sodium chloride, potassium chloride, sodium phosphate, ammonium bicarbonate, phosphate buffered saline.

The secondary diafiltration solution is used both to replenish solvent lost via the permeate on TFF permeate output line 1219 and/or to ensure that a predetermined number of diavolumes of the first retentate fucan composition and secondary diafiltration solution are circulated over the TFF filter 1210. By controlling second diafiltration solution valve 1234, the secondary diafiltration solution can be added in a pulse process. In other embodiments, the secondary diafiltration solution can be added in a continuous mode. The number of diavolumes of secondary diafiltration solution to process over TFF filter 1210 can be predetermined. The process can be continued for a predetermined period of time, for example between about 1 and about 6 hours, between about 3 and about 12 hours and between about 10 and about 24 hours. The process can be continued for a predetermined number of diavolumes of the chelating agent, for example between about 1 and about 4 diavolumes, between about 3 and about 6 diavolumes, between about 5 and about 10 diavolumes and between about 7 and about 20 diavolumes. for example a cationic content of below 10 parts per million (ppm), below 1 ppm, below 0.1 ppm and below 0.01 ppm multivalent cations. The process can be continued and the residual chelating agent concentration in the fucan container 1216 can be measured and the TFF process terminated when a suitably low residual chelating agent concentration has been attained, for example a residual chelating agent level of below 10 ppm, below 1 ppm, below 0.1 ppm and below 0.01 ppm. The resulting second retentate fucan composition in fucan container 1216 comprises the purified/modified fucan product of the process of cationic content modification system 1200. As desired, the resulting second retentate fucan composition in fucan container 1216 can be removed from fucan container 1216 via cationic content modification system output line 1208.

Super Critical Fluid Extraction

Fucans in a fucan composition such as a starting fucan composition containing undesirable levels of impurities undergoes a supercritical fluid extraction. The methods can comprise: providing the starting fucan composition as a solid; placing the starting fucan composition in a supercritical extractor; subjecting the starting fucan composition in the supercritical extractor to a suitable pressure above 70 bar; heating the starting fucan composition in the supercritical extractor to a suitable temperature above 30° C.; filling the supercritical extractor with a supercritical fluid to produce a purified/modified fucan and a supercritical fluid containing extracted impurities; removing the supercritical fluid containing extracted impurities from the supercritical extractor after a predetermined amount of time; and recovering the purified/modified fucan.

Filling the supercritical extractor with a supercritical fluid may comprise filling the supercritical extractor with carbon dioxide. The supercritical carbon dioxide can be supplemented with between 2% v/v and 10% v/v ethanol. In some embodiments, the supercritical carbon dioxide can be supplemented with approximately 5% v/v ethanol as a co-solvent. Alternative supercritical fluids to carbon dioxide for use with this method include but are not limited to ethanol, ethane, hydrochloric acid, hydrofluoric acid, sulfuric acid and nitric acid.

Subjecting the starting fucan to a suitable pressure may comprise subjecting the starting fucan composition to a pressure between about 70 bar and about 2000 bar. Subjecting the starting fucan composition to a suitable temperature may comprise subjecting the starting fucan composition to a temperature between about 30° C. and about 300° C.

Removing the supercritical fluid containing the extracted impurities after a predetermined amount of time may comprise removing the supercritical fluid after between about 5 minutes to about 50 hours, for example between about 10 minutes to about 1 hour, between about 30 minutes to about 5 hours, between about 1 hour to about 24 hours and between about 5 hours to about 48 hours.

The method may further comprise desalting the starting fucan composition before placing the starting fucan composition in a supercritical extractor. The desalting may comprise diafiltrating the starting fucan composition as a solution in water across a molecular weight cutoff (MWCO) tangential flow filtration (TFF) filter. The diafiltrating may comprise diafiltrating the starting fucan composition with distilled water. The molecular weight cutoff TFF filter can have a molecular weight cutoff smaller than a desired molecular weight separation point or target in or for the purified/modified fucan, for example a 50 kDa, 70 kDa, 100 kDa, 200 kDa, 300 kDa, 500 kDa or 1000 kDa molecular weight cut-off. The diafiltrating may further comprise pre-filtering the starting fucan composition in through a suitable pre-filter to remove particulate matter.

Chemical Structural Modification

The methods, systems etc. discussed herein can comprise chemical structural modification of the fucans, including the fucans in a fucan composition. The chemical structural modification may involve removal of functional groups from the fucan, for example, 0-acetyl, N-acetyl, methoxy, hydroxyl, carboxylic and/or sulfate functional groups from the fucan structure. The chemical structural modification may involve the use of a wide variety of chemical reagents, for example, acids, bases, detergents and/or oxidizing agents.

Tangential Flow Filtration

Some of the methods discussed herein utilize tangential flow filtration (TFF). Consistent with typical identification of tangential flow filtration (TFF) filters, the nominal molecular weight cut-off (MWCO) value for a given TFF filter will selectively retain on its retentate side a solution containing molecules that did not cross the filter barrier and thus generally have molecular weights and/or sizes greater than the molecular weight of molecules that do cross/permeate the barrier to the permeate side. Thus, molecular weight cut-off values for TFF filters are typically not absolute for any given polymer or nominal cut-off value: a given TFF filter will pass or retain some molecules both above and below the nominal molecular weight cut-off. The actual cut-off/selectively values and effects of a nominal TFF filter for a particular polymer can be routinely determined for the particular polymer.

A number of factors can affect the permeation behavior of the TFF filters. These factors may be dependent on the TFF filters themselves or dependent on an attribute of the target polymers, for example the folding behavior and folded structure of the target polymer can affect the behavior of the target polymer in crossing/not-crossing the TFF filter's MWCO barrier. Regarding the TFF filters themselves, as is known, a number of factors can affect the permeation behavior of the TFF filters. For example, manufacturing methods can cause a variety of hole sizes within the specific TFF filter, which variety can include holes both larger and smaller than the nominal MWCO. Thus, a TFF filter having a nominal molecular weight cut-off value will substantially pass/retain molecules at the nominal molecular weight cut-off value, but can also pass/retain some molecules below and/or above such value.

Gel Permeation Chromatography

Gel permeation chromatography was employed to evaluate the molecular weight distributions obtained for the experimental examples. There are a large number of different parameters, columns and standards available for use in gel permeation chromatography, resulting in a variety of instrumentation set-ups available for the analysis of molecular weight. For molecular weight determinations herein, the GPC were conducted using the following parameters: The mobile phase was 0.1M sodium nitrate run at 0.6 mL/min. The column compartment and detector were at 30° C. A Waters 2414 refractive index detector was used for detection.

Suitable GPC columns include GPC columns compatible with aqueous solvents, for example columns packed with at least one of sulfonated styrene-divinylbenzene, NH-functionalized acrylate copolymer network, modified silica and hydroxylated polymethacrylate-based gel. For the analyses herein, three columns were used in series, comprising one 40 mm long guard column with an inner diameter (ID) of 6 mm packed with 6 µm particle size hydroxylated polymethacrylate-based gel, followed by a first 300 mm analytical GPC column with a 7.8 mm ID packed with 12 µm particle size hydroxylated polymethacrylate-based gel that has an exclusion limit of about 7,000 kDa and an effective molecular weight range of between about 50 kDa and about 5,000 kDa, followed by a second 300 mm analytical GPC column with a 7.8 mm ID packed with 10 µm particle size hydroxylated polymethacrylate-based gel that has an exclusion limit of about 7,000 kDa and an effective molecular weight range of between about 1 kDa and about 6,000 kDa. The total effective molecular weight range of the column set up was between about 1 kDa and about 6,000 kDa. An example of this column set up can be Ultrahydrogel® guard-Ultrahydrogel® 2000-Ultrahydrogel® Linear columns connected in series.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

A molecular weight stated for a fucan/fucoidan polymer herein is a value of molecular weight about which there will always be a distribution of molecules of higher and lower molecular weights, increasing or decreasing in amount or percentage as the molecular weight increases or decreases away from the specified molecular weight. The distribution may, but is not required to, have a generally Gaussian or distorted Gaussian shape.

Results in the tables herein contain abbreviations used for certain characteristics of a molecular weight distribution. Gel permeation chromatography is denoted by GPC, peak retention time is denoted by PRT, peak molecular weight is denoted by PMW, weight average molecular weight is denoted by WAMW, number average molecular weight is denoted by NAMW, percentage distribution is denoted by % dist., molecular weight is denoted by MW, polydispersity index is denoted by PDI and molecular weight cutoff is denoted by MWCO.

Diseases and Conditions

Fibrous Adhesions

A fibrous adhesion is a type of scar that forms between two parts of the body, usually after surgery (surgical adhesion). Fibrous adhesions can cause severe problems. For example, fibrous adhesions involving the female reproductive organs (ovaries, Fallopian tubes) can cause infertility, dyspareunia and severe pelvic pain. Fibrous adhesions that occur in the bowel can cause bowel obstruction or blockage, and fibrous adhesions can also form in other places such as around the heart, spine and in the hand. In addition to surgery, fibrous adhesions can be caused for example by endometriosis, infection, chemotherapy, radiation, trauma and cancer.

A variety of fibrous adhesions are discussed in this document. Terms such as surgical adhesions, post-surgical adhesions, postoperative adhesions, adhesions due to pelvic inflammatory disease, adhesions due to mechanical injury, adhesions due to radiation, adhesions due to radiation treatment, adhesions due to trauma, and adhesions due to presence of foreign material all refer to adherence of tissues to each other due to a similar mechanism and are all included in the term fibrous adhesions.

Fibrous adhesion formation is a complex process in which tissues that are normally separated in the body grow into each other. Surgical adhesions (also known as post-surgical adhesions) develop from the otherwise normal wound healing response of the tissues to trauma and have been reported to occur in over two-thirds of all abdominal surgical patients (Ellis, H., *Surg. Gynecol. Obstet.* 133: 497 (1971)). The consequences of these fibrous adhesions are varied and depend upon the surgical site or other site, such as a disease site, involved. Problems may include chronic pain, obstruction of the intestines and even an increased risk of death after cardiac surgery (diZerega, G. S., *Prog. Clin. Biol. Res.* 381: 1-18 (1993); diZerega, G. S., *Fertil. Steril.* 61:219-235 (1994); Dobell, A. R., Jain, A. K., Ann. *Thorac. Surg.* 37: 273-278 (1984)). In women of reproductive age, fibrous adhesions involving the uterus, fallopian tubes or ovaries are estimated to account for approximately 20% of all infertility cases (Holtz, G., *Fertil. Steril.* 41: 497-507 (1984); Weibel, M. A. and Majno, G. *Am. J. Surg.* 126: 345-353 (1973)).

The process of fibrous adhesion formation initially involves the establishment of a fibrin framework and normal tissue repair. The normal repair process allows for fibrinolysis alongside mesothelial repair. However, in fibrous adhesion formation the fibrin matrix matures as fibroblasts proliferate into the network and angiogenesis occurs resulting in the establishment of an organized fibrous adhesion within about 3 to 5 days (Buckman, R. F., et al., *J. Surg. Res.* 21: 67-76 (1976); Raferty, A. T., *J. Anat.* 129: 659-664 (1979)). Inflammatory processes include neutrophil activation in the traumatized tissues, fibrin deposition and bonding of adjacent tissues, macrophage invasion, fibroblast proliferation into the area, collagen deposition, angiogenesis and the establishment of permanent fibrous adhesion tissues.

Various attempts have been made to prevent surgical adhesions. These involve pharmacological approaches targeted at influencing the biochemical and cellular events that accompany surgical traumas well as barrier methods for the separation of affected tissues. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (films, gels or solutions) aiming to minimize apposition of serosal surfaces, have all been attempted. Currently, preventive therapies also include prevention of fibrin deposition, reduction of inflammation (steroidal and non-steroidal anti-inflammatory drugs) and removal of fibrin deposits.

Interventional attempts to prevent the formation of post-surgical adhesions have included the use of hydroflotation techniques or barrier devices. Hydroflotation involves the instillation of large volumes of polymer solutions such as dextran (Adhesion Study Group, *Fertil. Steril.* 40:612-619 (1983)), or carboxymethyl cellulose (Elkins, T. E., et al., *Fertil. Steril.* 41:926-928 (1984)), into the surgical space in an attempt to keep the organs apart. Synthetic barrier membranes made from oxidized regenerated cellulose (e.g., Interceed™), polytetrafluoroethylene (Gore-tex surgical membrane) and fully resorbable membranes made from a modified hyaluronic acid/carboxymethylcellulose (HA/CMC) combination (Seprafilm™) have also been used to reduce post-surgical adhesion formation in both animals and humans (Burns, J. W., et al., *Eur. J. Surg.* Suppl. 577: 40-48 (1997); Burns, J. W., et al., *Fertil. Steril.* 66:814-821 (1996); Becker, J. M., et al., *J. Am. Coll. Surg.* 183:297-306 (1996)). The success of these HA/CMC membranes may derive from their ability to provide tissue separation during the peritoneal wound repair process when fibrous adhesions form. The membranes were observed to form a clear viscous coating on the injured tissue for 3-5 days after application, a time period that is compatible with the time course of post-surgical adhesion formation (Ellis, H., *Br. J. Surg.* 50: 10-16 (1963)). Unfortunately, limited success has been seen with these methods.

Peritonitis involves inflammation of the peritoneum. Peritonitis can cause severe problems. For example, abdominal pain, abdominal tenderness and abdominal guarding. Peritonitis may involve spontaneous, anatomic and/or peritoneal dialysis related inflammation. Peritonitis may involve an infection, for example, perforation of a hollow viscus, disruption of the peritoneum, spontaneous bacterial peritonitis, and systemic infections may result in infection and peritonitis. Peritonitis may also not involve an infection, for example, leakage of sterile body fluids into the peritoneum, and sterile abdominal surgery may result in peritonitis. Various attempts have been made to prevent and/or treat peritonitis. For example, general supportive measures such as intravenous rehydration, antibiotics, and surgery. There is an unmet need for compounds, compositions, methods and the like (including delivery approaches) to inhibit, or otherwise treat and/or prevent, peritonitis, preferably more effectively with few side effects.

The purified/modified fucans discussed herein can be used to treat fibrous adhesions in a patient and can be included as a component of, or be, a purified/modified fucan medical composition, medical device, combination or pharmaceutical product configured and can be composed to treat fibrous adhesions. For example, a purified/modified fucan medical composition or medical device comprising between about 0.02 mg/mL to about 100 mg/mL, for example 0.1 mg/mL, 0.2 mg/mL, 0.3 mg/mL, 0.5 mg/mL, 0.9 mg/mL, 1 mg/mL, 2.5 mg/mL, 5 mg/mL 7.5 mg/mL, of a purified/modified fucan herein dissolved in a physiological salt solution. The physiological salt solution can be, for example, Lactated Ringer's Injection USP (LRS), normal saline and physiological Dextran solution.

The purified/modified fucan medical compositions and medical devices, which can be liquid medical compositions and devices, herein can contain pharmaceutically acceptable excipients such as buffers, stabilizers, preservatives, adjuvants, etc. Such purified/modified fucan medical compositions and medical devices can be used to treat fibrous adhesions pre-, during, or post-surgery by administering between about 0.01 mL/kg (per kilogram bodyweight of the patient or target) to about 10 mL/kg or 15 mL/kg of the fucan medical compositions or devices in the preceding paragraph. Doses and device quantities include, for example, about 0.03 mL/kg, 0.1 mL/kg, 0.2 mL/kg, 0.4 mL/kg, 0.5 mL/kg, 0.6 mL/kg, 1 mL/kg, 1.2 mL/kg, 2 mL/kg, 3 mL/kg, 4 mL/kg, 5 mL/kg, 8 mL/kg, 10 mL/kg and 15 mL/kg of the purified/modified fucan medical composition or medical device to the surgical site of the patient. In further embodiments, such purified/modified fucan medical compositions and medical devices can be used to treat fibrous adhesions at any selected target site, for example lesions, abrasions, injury sites, surgical sites and post-surgical sites by administering between about 0.04 mg/kg or 0.1 mg/kg to about 25 mg/kg or 50 mg/kg. Some examples of such doses include, for example, about 0.04 mg/kg, 0.075 mg/kg, 0.1 mg/kg, 0.2 mg/kg, 0.5 mg/kg, 1 mg/kg, 1.3 mg/kg, 2 mg/kg, 3 mg/kg, 4 mg/kg, 5 mg/kg, 7.5 mg/kg, 8 mg/kg, 10 mg/kg, 15 mg/kg, 20 mg/kg, 25 mg/kg and 50 mg/kg of the fucans herein, including for example the purified/modified fucans herein, to the surgical site of the patient. The administering can be accomplished, for example, by instilling a liquid medical composition or medical device generally throughout the target area; directing the liquid medical composition or medical device at a specific location(s) within the target area; spraying the liquid medical composition or medical device generally or at a specific location(s) within the target area; or, spraying or otherwise delivering the liquid medical composition or medical device via an applicator, which can be a spray applicator through a trocar, catheter, endoscope or other minimally invasive device, onto a specific location(s) that a surgeon or other practitioner has identified as particularly susceptible to or concerning for development of fibrous adhesions. In another aspect, the administering can be done after opening of the surgical wound but before the surgical procedure; during the surgical procedure, or after the surgical procedure but before the surgical wound has been closed.

If desired, the liquid medical composition or medical device can also be administered after the surgery is completed (for example through a syringe and needle) and can be administered to non-surgical target sites as well. The surgical site of the patient can be, for example, at least one of the pelvic cavity, abdominal cavity, dorsal cavity, cranial cavity, spinal cavity, ventral cavity, thoracic cavity, pleural cavity, pericardial cavity, skin, joints, muscles, tendons and ligaments. The administering of the purified/modified fucan medical composition or medical device into the surgical site of the patient can be accomplished in less than about 15 minutes, 10 minutes, 8 minutes, 6 minutes, 5 minutes, 4 minutes, 3 minutes, 2 minutes, 1 minute, 45 seconds, 30 seconds, 20 seconds, 15 seconds, 10 seconds and 5 seconds.

Examples of administering the purified/modified fucan medical composition or medical device to a surgical site include without limitation administering the purified/modified fucan medical composition or medical device at the surgical site of a Cesarean section surgical procedure; a microvascular free flap reconstruction surgical procedure, a full thickness skin graft surgical procedure, a V-Y advancement flap surgical procedure, a fasciocutaneous rotation flap surgical procedure, an arthroplasty surgical procedure, a mastectomy surgical procedure, a sequestrectomy surgical procedure, a saucerization surgical procedure, an osteotomy surgical procedure, an osteoplasty surgical procedure, a patellectomy surgical procedure, a synovectomy surgical procedure, a capsulectomy surgical procedure, a tendon or ligament repair surgical procedure, a tenolysis surgical procedure, a tenotomy surgical, a fasciotomy surgical procedure, a meniscal repair surgical procedure, a vertebrectomy surgical procedure, a ethmoidectomy surgical procedure, a Caldwell Luc's operation surgical procedure, a dacryocystorhinostomy surgical procedure, a lysis nasal synechia surgical procedure, a thymectomy surgical procedure, a pneumonolysis surgical procedure, a pneumonectomy surgical procedure, thoracoplasty surgical procedure, a bilobectomy surgical procedure, a portal hypertension surgery surgical procedure, a splenectomy surgical procedure, a esophagectomy surgical procedure, a peritonitis surgery surgical procedure, a gastrectomy surgery surgical procedure, a jejunojejunostomy surgery surgical procedure, a laparoscopic cholecystectomy surgery surgical procedure, a laparoscopic common bile duct exploration surgical procedure, a gastroenterostomy surgical procedure, a bariatric surgery surgical procedure, a bowel resection & anastomosis surgical procedure, a segemental hepatectomy surgical procedure, a lobectomy surgical procedure, a pancreatomy surgical procedure, a pancreaticoduodenectomy surgical procedure, a tumor resection surgical procedure, a laparoscopic nephrectomy surgical procedure, a cystectomy surgical procedure, an abdominal or pelvic adhesion lysis surgical procedure, a hysterosalpingostomy surgical procedure, a salpingoplasty surgical procedure, an ectopic pregnancy laparoscopic surgery surgical procedure, a joint replacement surgery surgical procedure, a broken bone repair surgical procedure, a hysterectomy surgical procedure, a gallbladder removal surgical procedure, a heart bypass surgical procedure, an angioplasty surgical procedure, an atherectomy surgical procedure, a breast biopsy surgical procedure, a carotid endarterectomy surgical procedure, a cataract surgery surgical procedure, a coronary artery bypass surgical procedure, a dilation and curettage surgical procedure, a hernia repair surgical procedure, a lower back pain surgery surgical procedure, a partial colectomy surgical procedure, prostatectomy surgical procedure and a tonsillectomy surgical procedure, after opening the surgical wound, during surgery, before closing the surgical wound and/or after closing the surgical wound.

Cancers Generally

Cancer has been the second leading cause of death in the U.S. and accounts for over 20% of all mortalities. Cancer is a proliferative disease and is characterized by the uncontrolled division of certain cells, which may lead to the formation of one or more tumors. A number of methods are used to treat cancer, including surgery, radiation, chemotherapy and combinations thereof. Although surgery is a relatively common method used for some localized tumors, there is still a significant chance of tumor recurrence after tumor excision.

Treating cancers and other proliferative diseases has been limited by the potential for damage or toxicity to non-cancerous, healthy tissues. In radiation and surgical treatments, the procedure has been generally confined to and proximal to the tumor sites. However, there can be significant risk to patients undergoing surgical removal of cancerous tissues (e.g., in removal of prostate or brain tumors there can be a significant risk of non-repairable damage to surrounding vital tissues, for example via potential reduced need for resection of non-tumor tissues. Furthermore, in focused radiation treatment, which has been given as a first line treatment for prostate cancer, there are similar risks. In the chemotherapeutic treatment of cancer, the drug has been administered systemically, so that the whole body is exposed to the drug. These drugs are designed to be toxic to cancer cells, but they are also (generally) toxic to non-cancerous cells so that patients become quite ill when undergoing drug treatments for cancer. Through experience, oncologists are able to give doses of these drugs that may be tolerated by some patients. However, these doses are often not successful in treating cancers.

One problem with any method of treating cancer has been the local recurrence of the disease. For example, approximately 700,000 Americans are diagnosed with localized cancer annually (approximately 64% of all cancer patients) and almost half a million are treated using surgical methods. Unfortunately, 32% of patients treated with surgery relapse after the initial treatment (approximately 21% relapse at the initial surgical site and 11% at distant metastatic sites). Almost 100,000 patients die annually due to localized recurrence of cancer. This has been especially true in breast cancer where 39% of patients undergoing lumpectomy will experience local recurrence of the disease.

Staging is a method of judging the progress of the cancer (solid tumor) in a patient. A simplified approach puts patients into three groups or stages based on how far the cancer has advanced:

Stage 1: The cancer can be treated by surgically removing part of the organ. This is also known as the resectable stage.

Stage 2: The cancer has advanced past the point of being resectable but is still confined to the organ itself.

Stage 3: The tumor has spread to other organs.

Many cancers are treated with anti-proliferative agents including, for example, 5-fluorouracil (Efudex®), vinca alkaloids (for example, vincristine (Oncovin®)), anthracyclines (for example, doxorubicin (Adriamycin®)), cisplatin (Platinol-AQ®), gemcitabine hydrochloride (Gemzar®), methotrexate and paclitaxel. Some examples of the toxicities associated with the anti-proliferative agents, methotrexate and paclitaxel, are discussed elsewhere herein. Methotrexate has been used to treat several cancers including, for example, bladder, breast, cervical, head and neck, hepatic, lung, and testicular cancers. Paclitaxel has been used to treat several cancers including, for example, ovarian, breast, and non-small cell lung cancers (*Compendium of Pharmaceutical and Specialties Thirty-fifth Edition*, 2000).

Toxicities due to 5-fluorouracil can include cardiovascular toxicity such as myocardial ischemia; central nervous system toxicities such as euphoria, acute cerebellar syndrome and ataxia; dermatologic toxicities such as alopecia and dermatitis; gastrointestinal toxicities such as nausea, vomiting and oral or gastrointestinal ulceration; hematologic toxicities such as leukopenia, thrombocytopenia and anemia; hypersensitivity toxicities such as anaphylaxis and contact hypersensitivity; ocular toxicities such as increased lacrimation, photophobia and conjunctivitis; and, other toxicities such as fever. 5-fluorouracil has been used to treat many cancers including, for example, breast, colorectal, gastric, hepatic, bladder, head and neck, non-small cell lung, ovarian, pancreatic, and prostate cancers (*Compendium of Pharmaceutical and Specialties Thirty-fifth Edition*, 2000).

Toxicities due to vincristine include central nervous system toxicities such as seizures in children and hallucinations; dermatologic toxicity such as alopecia; extravasation toxicity such as vesicant; gastrointestinal toxicities such as nausea, vomiting, constipation and stomatitis; hematologic toxicity such as myelosuppression; neurologic toxicities such as peripheral neuropathy and autonomic neuropathy; ocular toxicities such as double vision, transient blindness and optic atrophy; renal/metabolic toxicities such as urinary retention, hyperuricemia and bladder atony; respiratory toxicity such as shortness of breath; and, other toxicity such as fever in children. This anti-proliferative agent has been used to treat several cancers including, for example, Hodgkin's disease, small cell lung, Wilm's tumor, and testicular cancers (*Compendium of Pharmaceutical and Specialties Thirty-fifth Edition*, 2000).

Toxicities due to doxorubicin include cardiovascular toxicities such as electrocardiographic abnormalities and cardiomyopathy; dermatologic toxicities such as alopecia and nail changes; extravasation hazard toxicity such as vesicant; gastrointestinal toxicities such and nausea, vomiting and stomatitis; genitourinary toxicity such as red coloration of urine; hematologic toxicity such as myelosuppression; hypersensitivity toxicities such as anaphylaxis and skin rash; ocular toxicity such as conjunctivitis; reproductive toxicity such as infertility; and, other toxicity such as hyperuricemia. This anti-proliferative agent has been used to treat several cancers including, for example, breast, small cell lung, and ovarian cancers (*Compendium of Pharmaceutical and Specialties Thirty-fifth Edition*, 2000).

Toxicities due to cisplatin include cardiovascular toxicity such as electrocardiographic changes; dermatologic toxicity such as hyperpigmentation; extravasation hazard toxicity such as irritant; gastrointestinal toxicities such as nausea and vomiting; hematologic toxicities such as myelosuppression and hemolytic anemia; hypersensitivity toxicity such as anaphylactic; neuromuscular toxicity such as peripheral neuropathy and acute encephalopathy; ocular toxicity such as retrobulbar neuritis; otologic toxicities such as hearing loss and tinnitus; renal/metabolic toxicities such as toxic nephropathy and hypokalemia; and, other toxicity such as infertility. This anti-proliferative agent has been used to treat several cancers including, for example, bladder, small cell lung, ovarian, testicular, brain, breast, cervical, head and neck, hepatoblastoma, and thyroid cancers (*Compendium of Pharmaceutical and Specialties Thirty-fifth Edition*, 2000). Toxicities due to gemcitabine hydrochloride include, for example, hematologic toxicities such as myelosuppression; gastrointestinal toxicities such as nausea, vomiting and stomatitis; hepatic toxicities such as transient elevations of serum transaminases; renal toxicities such as proteinuria, hematuria, hemolytic uremic syndrome and renal failure; dermatologic toxicity such as rash and alopecia; edema toxicities such as edema and peripheral edema; and, other toxicity such as fever. This anti-proliferative agent has been used to treat pancreatic and non-small cell lung cancers (*Compendium of Pharmaceutical and Specialties Thirty-fifth Edition*, 2000).

The present discussion comprises prevention or treatment of localized cancers or solid tumors that can be treated include those of the prostate, breast, pancreas, liver, kidney, genitourinary system, brain, gastrointestinal system, respiratory system, and head and neck. The compositions, etc., herein may prevent or treat cancers, including metastases, by allowing controlled release of purified/modified fucan at a site somewhat distant from the target tumors by allowing effective concentrations of the purified/modified fucan to reach the tumors and/or metastases by diffusion or even systemic transport. Some of these cancers are discussed further in the following paragraphs.

Prostate Cancer

Prostate cancer is a malignant tumor that arises in the cells lining the prostate gland. In the U.S., an estimated 200,000 patients will develop prostate cancer this year, and more than 30,000 will die of the disease. Prostate cancer has a death to new cases ratio of ~15%. The cancer may remain within the prostate, or it may spread to surrounding tissues or to distant sites (most often lymph nodes and bone). Usually prostate cancer spreads silently, producing symptoms only when it has progressed beyond the prostate. If prostate cancer has been diagnosed and treated during early stages, in some studies patients have had a 5-year survival rate of 94%.

Prostate cancer is often discussed as a disease of men over age 50. In fact, 80% of men with prostate cancer are 60 years of age and older. A man's chances of being diagnosed with prostate cancer during his lifetime are about 1 in 10, roughly the same as a woman's chances of having breast cancer. The number of reported new cases has risen dramatically in recent years as a result of improved tests that can detect the disease early in its development, often long before symptoms appear. The likelihood of developing prostate cancer in any given year increases with age but rises dramatically after age 50.

Current treatment options for prostate cancer depend upon the extent of disease progression, the patient's age and overall health. Elderly patients, who have only early stage cancer or who suffer from additional, more serious diseases, may be treated conservatively, whereas those whose cancer is advanced may undergo more aggressive treatment. Prostate cancer has been treated by various methods, including radiation therapy (external beam radiation or brachytherapy), hormone withdrawal or castration (surgical or chemical), anti-proliferative agents, surgery, and expectant therapy (that is, "watchful waiting"). No treatment guarantees an absolute cure, and some have considerable side effects.

Early stage prostate cancer (that is, the tumor is localized to the prostate) may be treated with "watchful waiting". Surgery for prostate cancer has been recommended for patients whose overall health has been otherwise good and the tumor is confined to the prostate gland. A common treatment for localized cancer of the prostate in men under the age of 70 has been radical prostatectomy (that is, surgical removal of the prostate).

Patients whose cancer is localized in the prostate area are commonly treated with external beam radiation (EBR). The radiation kills cancer cells and shrinks tumors. EBR accounts for less than 20% of localized prostate cancer treatment, with approximately 50% of these patients experiencing post radiation recurrences of the disease. Combined with early stage prostate cancer detection and increased demand from patients, brachytherapy (i.e., local radiation therapy) use has been expected to grow. In 1995, only 2.5% of newly diagnosed patients were treated using brachytherapy. Brachytherapy involves the implantation of radioactive metal "seeds" in the prostate tumor.

Treatment for prostate cancer that has spread involves removal of the testicles or hormone therapy. Both are used to inhibit or stop the production of the testosterone that has been driving the cancer growth. Approximately 20% of all prostate cancer patients undergo hormone withdrawal therapy. Hormone therapies include goserelin acetate (Zoladex®) or leuprolide acetate (Lupron®). Anti-proliferative agents used to treat prostate cancer have included 5-fluorouracil.

Breast Cancer

In the U.S., breast cancer has been the most common cancer among women, with about 180,000 new cases diagnosed every year (male breast cancer accounts for about 5% of all diagnosed breast cancers). It has been surpassed only by lung cancer as a cause of death in women, and it has been responsible for approximately 50,000 deaths annually. An American woman has a one in eight (or about 13%) chance of developing breast cancer during her lifetime. Over the past decade, most reported breast cancers were small, primary (arising independently; not caused by a metastasis) tumors. Roughly 70% to 80% of newly diagnosed patients exhibited early-stage disease (Stage 1 or 2), and a majority had no involvement of the axillary (underarm) lymph nodes.

Most breast cancers are carcinomas (that is, malignant tumors that grow out of epithelial tissues). Less than 1% of breast cancers are sarcomas, or tumors arising from connective tissue, bone, muscle or fat. In addition, most breast cancers (about 75%) are ductal carcinomas, arising in the tissues that line the milk ducts. A much smaller number of cancers (about 7%) are found within the breast lobules and are called lobular carcinomas. Paget's disease (cancer of the areola and nipple) and inflammatory carcinoma account for nearly all other forms of breast cancer.

Breast cancer treatment has been complicated and depends on many factors. Two important factors are the type of tumor and the stage of progression. Tumor characteristics, in particular, help to separate individuals into two groups: (1) those who are at low risk of cancer recurrence and (2) those who are at high risk of cancer recurrence. Specific prognostic factors place patients in either of these groups. These factors include tumor size; presence of female sex hormone estrogen and progesterone (ER/PR) receptors; cellular growth cycle phase (whether tumor cells are actively dividing or are in "S-phase"); presence of a protein known as "her-2-neu protein"; tumor grade, an indicator of tumor cell differentiation or change; and, tumor ploidy, the number of sets of genetic material within tumor cells.

Treatment of primary disease without significant lymph node involvement has been by lumpectomy and radiotherapy. More significant lymph node involvement may warrant mastectomy and removal of auxiliary lymph nodes. At this stage the chance of metastasis and local recurrence has been high. Treatment of metastatic disease has been palliative, involving radiation therapy and chemotherapy, which are immunosuppressive, cytotoxic and leukopenia. Anti-proliferative agents including, for example, 5-fluorouracil, doxorubicin, methotrexate, and paclitaxel, have been approved for use against breast cancer.

Pancreatic Cancer

The pancreas is an organ of the digestive system located near the stomach and small intestine. It has two major functions: the production of enzymes and hormones. Cancers of the pancreas can occur in the exocrine (i.e., enzymes) pancreas (e.g., classic pancreatic adenocarcinomas) or can occur in the endocrine (i.e., hormones) pancreas.

Cancers of the exocrine pancreas are a very serious health issue. In the U.S., approximately 28,000 patients are diagnosed with pancreatic cancer, while about the same number die annually from this disease. Pancreatic cancer occurs equally in males and females. Due to difficulties in diagnosis, the intrinsic aggressive nature of pancreatic cancers, and the sparse systemic treatment options available, only approximately 4% of patients diagnosed with pancreatic adenocarcinoma live for 5 years after diagnosis. Pancreatic cancer has been the $5^{th}$ leading cause of cancer death, following breast, lung, colon, and prostate cancer.

The choice of treatment for pancreatic cancer depends largely on the stage of the tumor. Possible treatments include surgery, anti-proliferative agents, radiation, and biological therapy. Surgery has been usually reserved for Stage 1 patients whose cancer is deemed resectable. Sometimes a combination of therapies, such as radiation and anti-proliferative agent given before or after surgery, can increase a patient's chances of survival. Pancreatic cancer that is deemed unresectable (usually Stage II or later) may be treated using anti-proliferative agents in clinical trials. Anti-proliferative agents, such as, for example, gemcitabine or 5-fluorouracil have had some effect against pancreatic cancer and gemcitabine has been used as a palliative agent. Toxicities due to these anti-proliferative agents are discussed elsewhere herein. Radiation therapy has some effect against pancreatic cancer when used in combination with chemotherapy. Radiation therapy alone may subdue symptoms. This form of treatment has also been used in Stage II or later pancreatic cancers.

Bladder Cancer

In 1998, it was estimated that over 54,000 new cases of bladder cancer would be diagnosed in the U.S. and about 15,000 deaths would be attributed to the disease. Bladder cancer has been the fourth most common cancer among American men and the ninth most common cancer among American women. It occurs three times more frequently in men than in women. Primarily a disease of older men, bladder cancer has been a significant cause of illness and death. The risk of bladder cancer increases steeply with age (80% of cases occur in people older than 50 years), with over half of all bladder cancer deaths occurring after age 70. In white men over 65, the annual disease rate of bladder cancer has been approximately 2 cases per 1,000 persons; this contrasts with a rate of 0.1 cases per 1,000 persons under 65. During one's lifetime, the probability of developing bladder cancer has been greater than 3%; however, the probability of dying, from bladder cancer has been small (<1%). Bladder cancer rarely occurs in people who are younger than 40 years of age.

Recent studies suggest that certain genes and inherited metabolic abilities may play a role in bladder cancer. Transitional cell carcinoma (TCC) has been the most common form of bladder cancer. TCC usually occurs as a superficial (surface), papillary (wart-like), exophytic (outward-growing) mass upon a stalk-like base. In some cases, though, TCC may be attached on a broad base or it may appear ulcerated (within an indented lesion). Papillary TCCs often start out as areas of hyperplasia that later dedifferentiate or lose individual cell characteristics. Only about 10% to 30% of papillary TCCs develop into invasive cancers. By contrast, nonpapillary forms of TCC are more likely to become invasive. As noted, such TCCs may appear ulcerated or flat. Flat, nonpapillary TCC that has been made up of anaplastic epithelium has been classified as carcinoma in situ (CIS or TIS). The tissue of CIS contains cells that are large, have noticeable nucleoli (round body within a cell; involved in protein synthesis), and lack normal polarity.

The treatment of bladder cancer depends upon many factors. The most important of these factors are the type of tumor that is present and its stage. Common treatments include transurethral resection (TUR), electrosurgery, laser surgery, intravesical therapy, anti-proliferative agents, surgical therapy, cystectomy, and radiation therapy. Examples of anti-proliferative agents used to treat bladder cancer include, for example, 5-fluorouracil, cisplatin and methotrexate. Toxicities due to the anti-proliferative agents, 5-fluorouracil, cisplatin, and methotrexate, are discussed elsewhere herein.

Brain Cancer

Brain tumors are often inoperable and more than 80% of patients die within 12 months of diagnosis. Approximately 18,000 new cases of primary intracranial (brain) cancer are diagnosed each year in the U.S. This represents about 2 percent of all adult cancers. More than 50 percent of these are high-grade gliomas (i.e., glioblastoma multiform and anaplastic astrocytoma tumors). Patients with these tumors often suffer from severe disabilities such as motor dysfunction, seizures, and vision abnormalities.

Tumors that begin in brain tissue are known as primary brain tumors. Primary brain tumors are classified by the type of tissue in which they begin. The most common brain tumors are gliomas, which begin in the glial (supportive) tissue. Others include astrocytomas, brain stem gliomas, ependymomas and oligodendrogliomas.

Surgical removal of brain tumors has been recommended for most types and in most locations and should be as complete as possible within the constraints of preservation of neurologic function. An exception to this rule has been for deep-seated tumors, such as pontine gliomas, which are diagnosed on clinical evidence and are treated without initial surgery approximately 50% of the time. In many cases, however, diagnosis by biopsy is performed. Stereotaxic biopsy can be used for lesions that are difficult to reach and resect. Patients who have brain tumors that are either infrequently curable or unresectable should be considered candidates for clinical trials that evaluate radiosensitizers, hyperthermia, or interstitial brachytherapy used in conjunction with external-beam radiation therapy to improve local control of the tumor or for studies that evaluate new drugs and biological response modifiers.

Radiation therapy has a major role in the treatment of most tumor types and can increase the cure rate or prolong disease-free survival. Radiation therapy may also be useful in the treatment of recurrences in patients treated initially with surgery alone. Chemotherapy may be used before, during, or after surgery and radiation therapy. Recurrent tumors are treated with chemotherapy as well. Anti-proliferative agents used in the treatment of brain cancers include cisplatin. Examples of the toxicities associated with this anti-proliferative agent are discussed elsewhere herein.

Restenosis

Restenosis is a form of chronic vascular injury leading to vessel wall thickening and loss of blood flow to the tissue supplied by the blood vessel. This inflammatory disease can occur in response to vascular reconstructive procedures including any manipulation that relieves vessel obstruction. Thus, restenosis has been a major restrictive factor limiting the effectiveness of these procedures.

The present discussion comprises prevention or treatment of restenosis, for example by administering to a blood vessel a therapeutically effective amount of the combination of an oligonucleotide therapeutic and an anti-inflammatory agent. Suitable compositions include a polymeric carrier that can be surgically implanted at a restenosis site, or potential restenosis site, or can be injected via a catheter as a polymeric paste or gel. Suitable compositions may comprise purified/modified fucans discussed herein.

Arthritis

Rheumatoid arthritis (RA) is a debilitating chronic inflammatory disease characterized by pain, swelling, synovial cell proliferation (pannus formation) and destruction of joint tissue. In the advanced stage, the disease often damages critical organs and may be fatal. The disease involves multiple members of the immune system (macrophages/monocytes, neutrophils, B cells and T cells) complex cytokine interactions and synovial cell malfunction and proliferation. Early aggressive treatment has been recommended with disease modifying anti-rheumatic drugs (DMARDs) such as methotrexate, which drug is discussed elsewhere herein.

Crystal induced arthritis has been characterized by crystal induced activation of macrophages and neutrophils in the joints and is followed by excruciating pain for many days. The disease progresses so that the intervals between episodes gets shorter and morbidity for the patient increases. This disease has been generally treated symptomatically with non-steroidal anti-inflammatory drugs (NSAIDs) such as diclofenac sodium (Voltaren®). This anti-inflammatory agent has toxicities which include central nervous system toxicities such as dizziness and headache; dermatologic toxicities such as rash and pruritus; gastrointestinal toxicities such as exacerbated ulcerative colitis and Crohn's disease; genitourinary toxicities such as acute renal failure and renal papillary necrosis; hematologic toxicities such as agranulocytosis, leukopenia and thrombocytopenia; hepatic toxicities such as elevated liver transaminases and hepatitis; and, other toxicities such as asthma and anaphylaxis.

The present discussion comprises prevention or treatment of rheumatoid arthritis, for example via administering to a patient a therapeutically effective amount of an oligonucleotide therapeutic and optionally an anti-inflammatory agent. Suitable compositions include a polymeric carrier that can be injected into a joint as a controlled release carrier of the anti-inflammatory agent and microparticulates as controlled release carriers of the oligonucleotide therapeutic (which in turn has been incorporated in the polymeric carrier). Suitable compositions may comprise purified/modified fucans discussed herein. Such polymeric carriers may take the form of polymeric microspheres, pastes or gels.

Inflammatory Conditions

The compositions, etc., herein may optionally inhibit or treat inflammatory conditions involving neutrophils for example comprising administering to a patient compositions containing an oligonucleotide therapeutic and an anti-inflammatory agent. Examples of such conditions include crystal-induced arthritis; osteoarthritis; non-rheumatoid inflammatory arthritis; mixed connective tissue disease; Sjögren's syndrome; ankylosing spondylitis; Behçet's syndrome; sarcoidosis; psoriasis; eczema; inflammatory bowel disease; chronic inflammatory lung disease; neurological disorders; and, multiple sclerosis. Some of these diseases are discussed further in the following paragraphs.

Chronic Inflammatory Skin Diseases (Including Psoriasis and Eczema)

Psoriasis is a common, chronic inflammatory skin disease characterized by raised, thickened and scaly lesions which itch, burn, sting and bleed easily. While these diseases have cellular proliferation and angiogenic components in later stages of the disease, patients often have accompanying arthritic conditions. Symptoms may be treated with steroidal anti-inflammatory agents such as prednisone or anti-proliferative agents such as methotrexate, which agents are discussed elsewhere herein. The compositions herein may also be used to inhibit or otherwise treat and/or prevent chronic inflammatory skin diseases, for example psoriasis and/or eczema.

The following provides some additional representative examples of inflammatory diseases that can be treated with compositions discussed herein, include, for example, arterial embolization in arteriovenous malformations (vascular malformations); menorrhagia; acute bleeding; central nervous system disorders; and, hypersplenism; inflammatory skin diseases such as psoriasis; eczematous disease (atopic dermatitis, contact dermatitis, eczema); immunobullous disease; and, inflammatory arthritis which includes a variety of conditions including rheumatoid arthritis, mixed connective tissue disease, Sjögren's syndrome, ankylosing spondylitis, Behçet's syndrome, sarcoidosis, crystal induced arthritis and osteoarthritis (all of which feature inflamed, painful joints as a prominent symptom).

Ischemia

Ischemia or ischaemia involves a restriction in blood supply, which may include a shortage of supply of oxygen, glucose and other components required for proper tissue function, resulting in damage and/or dysfunction of tissue. Ischemia can cause severe problems. For example, tissues can become anoxic, necrotic, and clots can form. Various attempts have been made to prevent and/or treat ischemia. For example, restoration of blood flow, or reperfusion. Restoration of blood, however, involves the reintroduction of oxygen, which can cause additional damage due to the production of free radicals, resulting in reperfusion injury. Reperfusion injury can cause severe problems. The compositions herein may be used to inhibit or otherwise treat and/or prevent, ischemia, and/or reperfusion injury.

Endotoxemia

Endotoxemia is the presence of endotoxins in the blood. Endotoxemia can cause severe problems. For example, endotoxemia can lead to septic shock. The compositions herein may be used to inhibit, or otherwise treat and/or prevent, endotoxemia.

Keloid Scarring

Keloid trait causes wounds to heal with raised scars. Keloid traits' raised scars involve abnormal fibrous scarring. Keloid trait causes severe problems, for example, pain and disfigurement. The compositions herein may be used to inhibit, or otherwise treat and/or prevent, keloid trait and its resulting raised scars.

Keloid (keloid scar) is a type of scar that expands in growths over normal skin. Keloids involve abnormal collagen growth, including type I and type III collage abnormal growth. Keloids cause severe problems, for example, pain, itchiness, and if infected may ulcerate. Attempts have been made to treat or prevent keloids including the use of surgery, dressings, steroid injections and laser therapy. The compositions herein may be used to inhibit, or otherwise treat and/or prevent, keloids.

Dermatitis

Dermatitis includes inflammation of the skin including atopic dermatitis and contact dermatitis. For example, contact dermatitis involves localized rash and/or irritation of the skin following contact of the skin with a foreign substance. For example, atopic dermatitis is a chronically relapsing, pruritic skin disease. Atopic dermatitis is sometimes called prurigo Besnier, neurodermitis, endogenous eczema, flexural eczema, infantile eczema, childhood eczema and prurigo diathsique. Eczema is a disease in a form of dermatitis. Other types of dermatitis include spongiotic dermatitis, seborrhoeic dermatitis (dandruff), dyshidrotic dermatitis (pompholyx), urticaria, vesicular dermatitis (bullous dermatitis), and popular urticaria. Dermatitis can cause severe problems. For example, dry skin, skin rashes, skin edema, skin redness, skin itchiness, skin crusting, cracking, blistering, oozing and bleeding. Attempts have been made to treat or prevent dermatitis including the use of corticosteroids and coal tars. The compositions herein may be used to inhibit, or otherwise treat and/or prevent, dermatitis including atopic dermatitis, eczema, contact dermatitis, spongiotic dermatitis, seborrhoeic dermatitis, dyshidrotic dermatitis, urticaria, vesicular dermatitis, and popular urticaria.

Rosacea

Rosacea is a chronic disease or condition typically characterized by facial erythema. Rosacea can cause severe problems. For example, rosacea typically begins as redness on the forehead, nose or cheeks and can also cause redness on the neck, ears, scalp and chest. For example, rosacea can cause additional symptoms including telangiectasia, papules, pustules, painful sensations, and in advanced cases rhinophyma (red lobulated nose) may develop. Rosacea subtypes include erythematotelangiectatic rosacea, papulopustular rosacea, phymatous rosacea, and ocular rosacea. Attempts have been made to treat or prevent rosacea including the use of anti-inflammatories and antibiotics. The compositions herein may be used to inhibit, or otherwise treat and/or prevent, rosacea including its erythematotelangiectatic, papulopustular, rosacea and ocular subtypes.

Medical Device, Medical Materials, Combination, and Pharmaceutical Products

The discussion herein also provides medical devices, combination, and pharmaceutical products, comprising compositions as discussed herein in a medical device, combination product or pharmaceutically acceptable container. The products can also include a notice associated with the container, typically in a form prescribed by a governing agency regulating the manufacture, use, or sale of medical devices, combination, and pharmaceuticals or biopharmaceuticals, whereby the notice is reflective of approval by the agency of the compositions, such as a notice that a purified/modified fucan has been approved as an anti-proliferative agent or anti-inflammatory agent, e.g., for human or veterinary administration to treat proliferative diseases or inflammatory diseases (such as, for example, inflammatory arthritis, restenosis, surgical adhesions, psoriasis and peritonitis). Instructions for the use of the purified/modified fucan herein may also be included. Such instructions may include information relating to the dosing of a patient and the mode of administration.

The present application is further directed to methods of making the various elements of the purified/modified fucan, systems etc., discussed herein, including making the compositions themselves, as well as to methods of using the same, including for example treatment of the conditions, diseases, etc., herein.

The present application further comprises medical devices, medical materials, medical combination products, and pharmaceutical products for treatment of fibrous adhesions, arthritis, psoriasis or other diseases as desired comprising the purified/modified fucan and fucan compositions presented herein. The materials, etc., can be used in a medicament for treating fibrous adhesions, such as a surgical adhesions, arthritis, psoriasis or other diseases as desired. Also provided are methods of manufacturing and using such medicaments able to reduce symptoms associated with at least one of fibrous adhesions, arthritis, and psoriasis in a patient including a human patient, comprising combining a pharmaceutically effective amount of a fucan such as fucoidan as discussed herein with a pharmaceutically acceptable excipient or buffer.

The following Examples provide exemplary discussions of certain embodiments herein but the disclosure and claims are not limited thereto.

Example 1: Chemical Structural Modification

An exudate-extract was obtained from *Laminaria hyperborea*. The exudate-extract was filtered and small molecules were removed by tangential flow filtration (TFF) over a 100 kDa filter. A sample of the resulting retentate was lyophilized to obtain otherwise unmodified sample A. The resulting retentate was brought to 0.25 M NaOH by addition of 10 M NaOH solution and left at room temperature for 16 hours. The resulting sample was then centrifugally filtered over a 50 kDa filter and the resulting retentate collected and lyophilized to obtain base-treated sample B. Both unmodified sample A and base-treated sample B were analyzed by proton nuclear magnetic resonance spectroscopy ($^1$H-NMR) and the resulting $^1$H-NMR spectrum are shown in FIG. 2A.

Figure 2A:
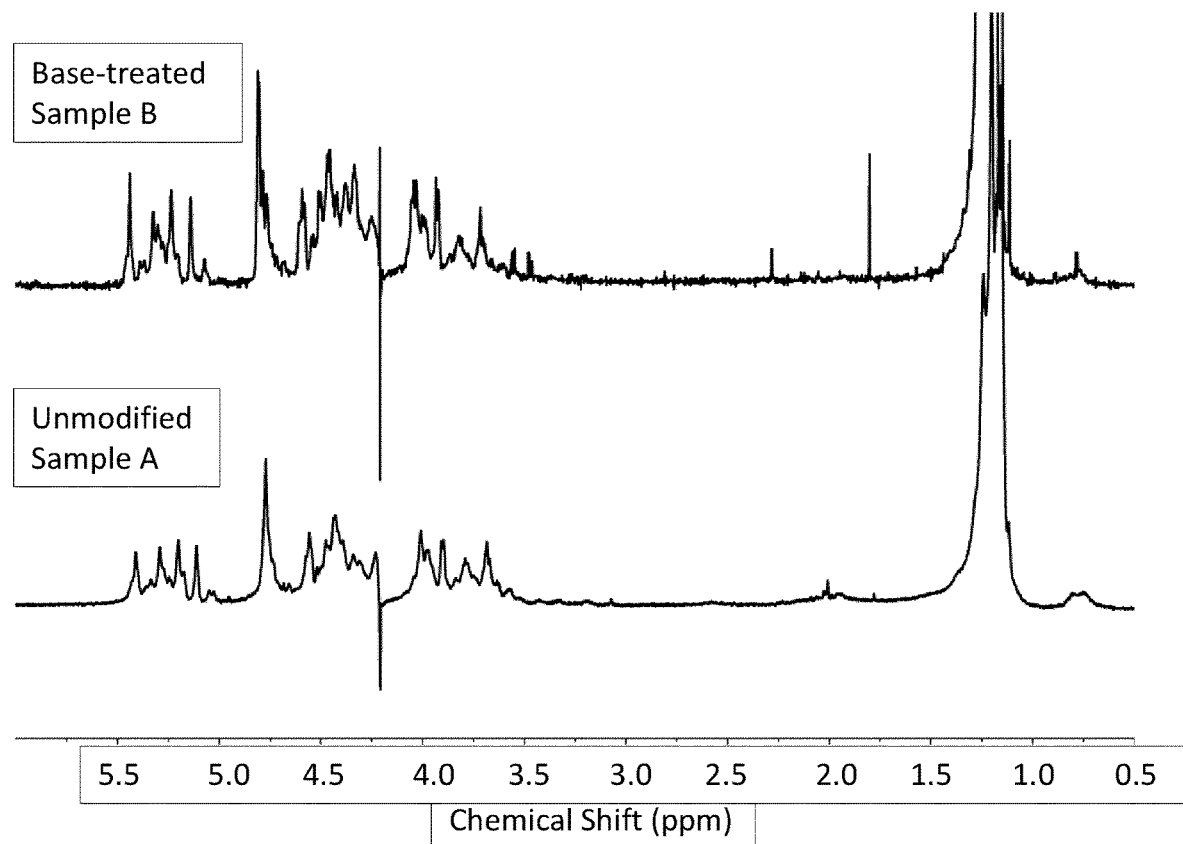
FIG. 2A depicts NMR results demonstrating that certain fucans treated according to methods herein undergo structural changes to the fucans.

FIG. 2A demonstrates the chemical structural modification of the fucan: the broad peak with a chemical shift about 2.0 ppm that is present in the unmodified sample A is not present in the base-treated sample B.

Unmodified sample A and base-treated/modified sample B were further analyzed by 2D $^1$H-$^{13}$C heteronuclear multiple quantum coherence (HMQC). The HMQC spectra, shown in FIG. 2B, were acquired at 70° C. with solvent signal suppression on a 600 MHz spectrometer equipped with 5-mm cold probe. A high number of scans of the HMQC spectra were acquired in the range from 10-30 ppm in the carbon dimension in 8 increments of 256-512 scans each; such scans were combined to create the spectra in FIG. 2B.

Figure 2B:
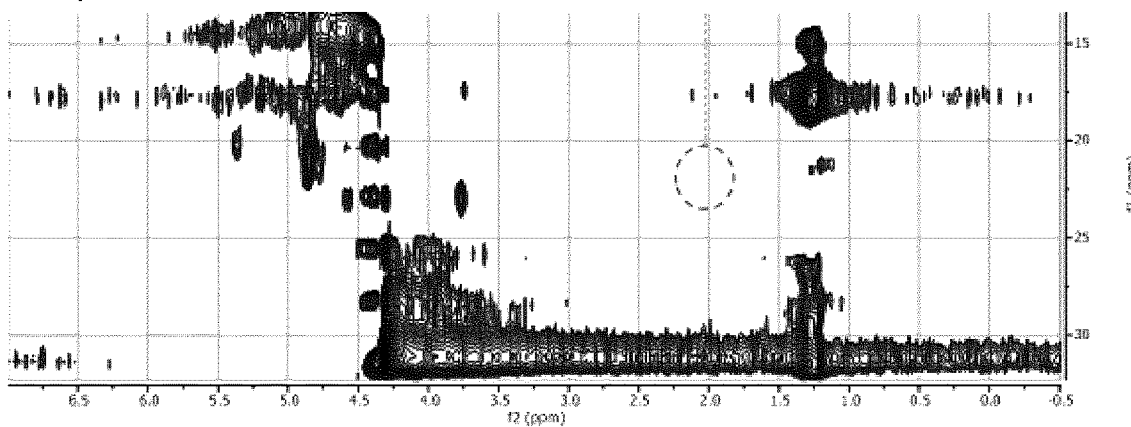
FIG. 2B depicts 2-D NMR results demonstrating that certain fucans treated according to methods herein undergo structural changes to the fucans.
Figure 2B:
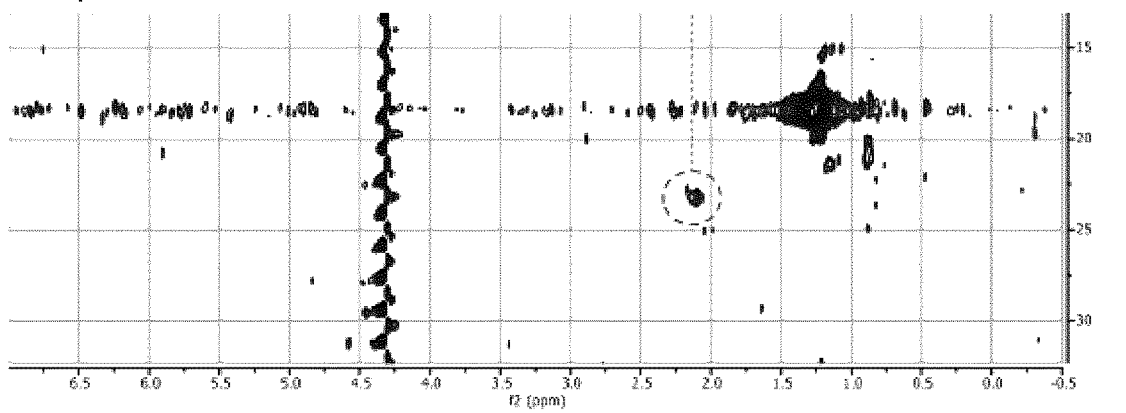

The HMQC spectra for unmodified sample A has a cross-peak corresponding to 0-acetyl groups, indicated by the signal circled in FIG. 2B. This cross-peak is not present in the spectra for base-treated sample B. This demonstrates the removal of acetyl groups from the fucan, and thus chemical structural modification of the fucan in base-treated sample B by the NaOH treatment.

Example 2: Physically Induced Flocculation

A brown powder-feedstock fucoidan was dissolved at about 10% w/v in distilled water to obtain a starting solution. Sodium chloride was added to the starting solution, to produce a mixture with a final sodium chloride concentration of about 0.1 M. The mixture was heated to near boiling for between 10-15 minutes. Treatment of the mixture at this temperature induced flocculation of suspended impurities and particulate non-fucoidan matter. The mixture was centrifuged at 2300 gravities for 40 minutes to separate the fucoidan containing solution from the flocculated non-fucoidan components. The fucoidan containing solution was visually inspected and a visual decrease in particulate matter and color was observed. A lyophilized portion of the fucoidan containing solution comprised an off-white powder with significantly less color than the feedstock fucoidan used. The loss of color can be quantified and compared, for example, by obtaining a ultraviolet/visible (UV/Vis spectrum) of the feedstock fucoidan at 10 mg/mL in water and a UV/Vis spectrum of the purified/modified fucan at 10 mg/mL in water, determining the total absorbance in the visible region of the spectrum, which is between about 400 nm and about 700 nm, and observing a decrease of about at least 5%, 10% or 20% in total absorbance in the purified/modified fucan relative to the feedstock fucoidan.

Example 3: Solid Phase Extraction

A brown powder-feedstock fucoidan was added to a 40 degrees Celsius mixture of 0.5 M NaOH in 70% v/v ethanol/water. The resulting reaction mixture was stirred and maintained at 40 degrees Celsius for 2 hours. The reaction mixture was then centrifuged to separate the solid purified/modified fucoidan from the 0.5 M NaOH in 70% v/v ethanol/water supernatant containing the extracted impurities.

The solid purified/modified fucoidan was found to be contain noticeably less color to the human eye than the feedstock fucoidan when visualized. This loss of color indicated the removal of impurities, such as phlorotannins, because fucans do not contain a chromophore and so will be colorless when completely pure. The loss of color can be quantified and compared, for example, by obtaining a ultraviolet/visible (UV/Vis spectrum) of the feedstock fucoidan at 10 mg/mL in water and a UV/Vis spectrum of the purified/modified fucan at 10 mg/mL in water, determining the total absorbance in the visible region of the spectrum, which is between about 400 nm and about 700 nm, and observing a decrease of about at least 5%, 10% or 20% in total absorbance in the purified/modified fucan relative to the feedstock fucoidan.

also hydrolyzed in 3M HCl at 90 degrees Celsius and analyzed by High Performance Anion Exchange—Pulsed Amperometry Detection (HPAE-PAD) for the detection of total carbohydrates and assessment of the removal of laminarin and alginate. Quantification of the impurities was against standards of monomeric glucose to assess removal of laminarin and monomeric mannuronic acid and monomeric guluronic acid to assess the removal of alginates.

Analysis results from the starting fucoidan and the resulting purified/modified fucans are presented in table 1 below.

TABLE 1

| | Analytical results of starting fucoidan and treated solutions | | | |
|---|---|---|---|---|
| Flocculation Treatment | Visual appearance | Alginate by HPAE-PAD | Starch by HPAE-PAD | UV/Vis signal 300-800 nm |
| Starting fucoidan | Brown solid, opaque brown in solution | None detected | None detected | 670.587* |
| Treated fucoidan | Light brownish yellow clear solution | None detected | None detected | 9.616 |

*Values determined via a representative starting fucoidan

Example 4: Chemically Induced Precipitation

A feedstock fucoidan composition was dissolved at 15% w/v in distilled water to form a starting solution. The starting solution was found to contain suspended particulates by observation. Calcium chloride was added to the starting solution to a level of 0.5 M to produce a reaction mixture. To simulate known impurities in natural fucoidan, sodium alginate was added at a concentration of 5% w/w alginate/fucoidan and starch was added at a concentration of 5% w/w starch/fucoidan. Starch was used as a mimetic for laminarin in this case. 10 M NaOH was added dropwise to the reaction mixture to bring the pH to between 7 and 8. This was done to avoid degradation of the fucoidan in the reaction mixture. A minimal amount of 10 M NaOH was again added to the reaction mixture to avoid the acidification of the reaction mixture from the subsequent addition of phosphoric acid. The reaction mixture was brought to 0.5 M phosphate through the addition of phosphoric acid. This initiated flocculation of the suspended particulates and precipitated impurities via the action of the calcium phosphate formed by the reaction of the calcium chloride with the phosphoric acid. The reaction mixture was allowed to stand at room temperature for 10 minutes to allow the flocculation to continue. The reaction mixture was centrifuged at 17568 gravities for 17 minutes to separate the desired purified fucoidan in a supernatant solution from the flocculated impurities. The supernatant solution was visually inspected to qualitatively assess the removal of color and particulate. An aliquot of the supernatant solution was also analyzed by UV/Vis absorption in the 300-800 nm region to assess the removal of non-fucoidan components that scatter light and/or absorb light in the UV/Vis spectral region. An aliquot of the supernatant solution was also lyophilized to obtain the fucan content. An aliquot of the supernatant solution was

Example 5: Chemically Induced Precipitation

A feedstock fucoidan composition was dissolved at 15% w/v in distilled water to form a starting solution. The starting solution was found to contain suspended particulates by observation. To simulate known impurities in natural fucoidan, sodium alginate was added at a concentration of 5% w/w alginate/fucoidan and starch was added at a concentration of 5% w/w starch/fucoidan. Starch was used as a mimetic for laminarin in this case. 10 M NaOH was added dropwise to the starting solution to bring the pH to between 7 and 8. This was done to avoid degradation of the fucoidan in the solution in case the subsequent addition of aluminum sulfate were to render the starting solution acidic. The starting solution was brought to 0.1 M aluminum sulfate to produce a reaction mixture. This initiated precipitation of impurities as well as flocculation of impurities and suspended particulates by the simultaneously formed aluminum hydroxide. The reaction mixture was allowed to stand at room temperature for 10 minutes to allow the flocculation to continue. The reaction mixture was centrifuged at 17568 gravities for 17 minutes to separate the desired purified fucoidan in a supernatant solution from the flocculated impurities. The supernatant solution was visually inspected to qualitatively assess the removal of color and particulate. An aliquot of the supernatant solution was also analyzed by UV/Vis absorption in the 300-800 nm region to assess the removal of non-fucoidan components that scatter light and/or absorb light in the UV/Vis spectral region. An aliquot of the supernatant solution was also lyophilized to obtain the fucan content. An aliquot of the supernatant solution was also hydrolyzed in 3M HCl at 90 degrees Celsius and analyzed by High Performance Anion Exchange—Pulsed Amperometry Detection (HPAE-PAD) for the detection of total carbohydrates and assessment of the removal of laminarin and alginate. Quantification of the impurities was against standards of monomeric glucose to assess removal of laminarin and monomeric mannuronic acid and monomeric guluronic acid to assess the removal of alginates.

Analysis results from the starting fucoidan and the resulting purified/modified fucans are presented in table 2 below.

TABLE 2

Analytical results of starting fucoidan and treated solutions

| Flocculation Treatment | Visual appearance | Alginate by HPAE-PAD | Starch by HPAE-PAD | UV/Vis signal 300-800 nm |
|---|---|---|---|---|
| Starting fucoidan | Brown solid, opaque brown in solution | None detected | None detected | 670.587* |
| Treated fucoidan | Light yellow clear solution | None detected | None detected | 15.188 |

*Values determined via a representative starting fucoidan

Example 6: Chemically Induced Precipitation

A starting fucoidan composition was dissolved at 15% w/v in distilled water to form a starting solution. The starting solution was found to contain suspended particulates by observation. To simulate known impurities in natural fucoidan, sodium alginate was added at a concentration of 5% w/w alginate/fucoidan and starch was added at a concentration of 5% w/w starch/fucoidan. Starch was used as a mimetic for laminarin in this case. Calcium chloride was added to the starting solution to a level of 0.5 M to produce a reaction mixture. This initiated the precipitation of the alginate. 10 M NaOH was added dropwise to the reaction mixture to bring the pH to between 7 and 8. This was done to avoid degradation of the fucoidan in the reaction mixture. The reaction mixture was brought to 0.5 M aluminum sulfate. This initiated flocculation of the suspended particulates, calcium alginate precipitate and other impurities via the action of calcium sulfate formed by the reaction of calcium chloride with aluminum sulfate and by the action of aluminum hydroxide formed from the aluminum sulfate in the reaction mixture. The reaction mixture was allowed to stand at room temperature for 10 minutes to allow the flocculation to continue. The reaction mixture was centrifuged at 17568 g for 17 minutes to separate the desired purified fucoidan in a supernatant solution from the flocculated impurities. The supernatant solution was visually inspected to qualitatively assess the removal of color and particulate. An aliquot of the supernatant solution was also analyzed by UV/Vis absorption in the 300-800 nm region to assess the removal of non-fucoidan components that scatter light and/or absorb light in the UV/Vis spectral region. An aliquot of the supernatant solution was also lyophilized to obtain the fucan content. An aliquot of the supernatant solution was also hydrolyzed in 3M HCl at 90 degrees Celsius and analyzed by High Performance Anion Exchange—Pulsed Amperometry Detection (HPAE-PAD) for the detection of total carbohydrates and assessment of the removal of laminarin and alginate. Quantification of the impurities was against standards of monomeric glucose to assess removal of laminarin and monomeric mannuronic acid and monomeric guluronic acid to assess the removal of alginates.

Analysis results from the starting fucoidan and the resulting purified/modified fucans are presented in table 3 below.

TABLE 3

Analytical results of starting fucoidan and treated solutions

| Flocculation Treatment | Visual appearance | Alginate by HPAE-PAD | Starch by HPAE-PAD | UV/Vis signal 300-800 nm |
|---|---|---|---|---|
| Starting fucoidan | Brown solid, opaque brown in solution | None detected | None detected | 670.587* |
| Treated fucoidan | Light yellow clear solution | None detected | None detected | 23.814 |

*Values determined via a representative starting fucoidan

Example 7: Liquid-Liquid Extraction

A starting fucan composition containing impurities is dissolved at 10 mg/mL in distilled water to produce an aqueous starting solution. 20% v/v heptane is added to the aqueous starting solution containing the starting fucoidan composition and the organic-aqueous mixture is then mixed at high shear for 30 minutes. The mixing is terminated, and the organic-aqueous mixture placed in a separatory funnel for the separation of the organic phase from the aqueous phase. The denser aqueous phase containing the desired fucan component settles to the bottom of the separatory funnel while the less dense organic phase containing impurities is present at the upper end of the separatory funnel. The organic-aqueous mixture is allowed to sit in the separatory funnel for 10 minutes. The aqueous phase is then decanted and collected as the desired purified/modified fucan in solution. The purified/modified fucan in solution can be found to contain between about 30%, 50%, 70% to about 100% less lipids, fatty acids, phlorotannin, proteins, fucoxanthin and/or chlorophyll than the starting fucan composition.

Example 8: Liquid-Liquid Extraction

A starting fucan composition containing impurities is dissolved at 10 mg/mL in distilled water to produce an aqueous starting solution. 20% v/v 1-butanol is added to the aqueous starting solution containing the starting fucoidan composition and the organic-aqueous mixture is then mixed at high shear for 30 minutes. The mixing is terminated, and the organic-aqueous mixture placed in a separatory funnel for the separation of the organic phase from the aqueous phase. The denser aqueous phase containing the desired fucan component settles to the bottom of the separatory funnel while the less dense organic phase containing impurities is present at the upper end of the separatory funnel. The organic-aqueous mixture is allowed to sit in the separatory funnel for 10 minutes. The aqueous phase is then decanted and collected as the desired purified/modified fucan in solution. The purified/modified fucan in solution can be found to contain between about 30%, 50%, 70% to about 100% less lipids, fatty acids, phlorotannin, proteins, fucoxanthin and/or chlorophyll than the starting fucan composition.

Example 9: Liquid-Liquid Extraction

A starting fucan composition containing impurities is dissolved at 10 mg/mL in distilled water to produce an aqueous starting solution. 20% v/v ethyl acetate is added to the aqueous starting solution containing the starting fucoidan composition and the organic-aqueous mixture is then mixed at high shear for 30 minutes. The mixing is terminated, and the organic-aqueous mixture placed in a separatory funnel for the separation of the organic phase from the aqueous phase. The denser aqueous phase containing the desired fucan component settles to the bottom of the separatory funnel while the less dense organic phase containing impurities is present at the upper end of the separatory funnel. The organic-aqueous mixture is allowed to sit in the separatory funnel for 10 minutes. The aqueous phase is then decanted and collected as the desired purified/modified fucan in solution. The purified/modified fucan in solution can be found to contain between about 30%, 50%, 70% to about 100% less lipids, fatty acids, phlorotannin, proteins, fucoxanthin and/or chlorophyll than the starting fucan composition.

Example 10: Diafiltration

A starting solution comprising about 8% w/v or a starting fucoidan composition was provided. The starting solution was filtered through a 0.22 micron filter. The cationic content in an aliquot of the filtered starting solution were determined by inductively coupled plasma mass spectrometry (ICP-MS) and found to contain above 0.01% w/w aluminum/fucan, above $10^{-5}$% w/w arsenic/fucan and above 0.01% w/w calcium/fucan, all being undesirable levels of each respective cation. The starting solution was diafiltered for 4 diavolumes with 0.1 M EDTA, 0.01 M NaOH solution. The resulting retentate fucoidan solution was then diafiltered with about 2.5 diavolumes of 5 mM $Na_2SO_3$, 5 mM NaCl solution. The resulting secondary retentate fucoidan solution was assayed for cationic content by ICP-MS. The results for the starting fucoidan composition and the resulting purified/modified fucan are shown in Table 4 below.

TABLE 4

Analytical results of starting fucoidan and treated solutions

| Treatment | % w/w Al/fucoidan | % w/w As/fucoidan | % w/w Ca/fucoidan | % w/w Mg/fucoidan |
|---|---|---|---|---|
| Input | $2.95 \times 10^{-1}$ | $1.79 \times 10^{-5}$ | $2.78 \times 10^{-2}$ | $4.76 \times 10^{-3}$ |
| Purified/modified Fucan | $3.33 \times 10^{-4}$ | $<4.38 \times 10^{-6}$ | $3.85 \times 10^{-3}$ | $1.70 \times 10^{-3}$ |

Example 11: Super Critical Fluid Extraction

A solid starting fucoidan composition of about 100 g is provided. The solid is placed in a supercritical extractor. The extractor is pressurized to 5800 psi and heated to 50 degrees Celsius and then purged with supercritical carbon dioxide at 100 mL/minute for 3 hours. The supercritical carbon dioxide is purged from the extractor and the solid modified/purified fucoidan collected and analyzed for impurities. The collected solid modified/purified fucoidan can be found to contain between about 30% to about 100% less lipids, fatty acids, phlorotannins, laminarins, alginates, proteins, Maillard reaction products, fucoxanthin, chlorophyll, free ions, bacteria and/or DNA than the starting fucoidan composition.

Example 12: Chemically Induced Precipitation, Lysis and Flocculation

A starting fucoidan composition, found to contain about 0.70% w/w total nitrogen, was dissolved at 15% w/v in distilled water to form a starting solution. The presence of total nitrogen indicates the presence of undesired impurities, for example, cellular components, DNA, proteins and bacteria. A reduction in the total nitrogen indicates that these nitrogen-containing impurities have been removed from the starting fucoidan composition or from the fucoidan polymers, as the case may be, because the nitrogen containing impurities may be chemically or ionically bound to such fucoidan molecules.

The starting solution was found to contain suspended particulates by observation. Calcium chloride was added to the starting solution to a level of 0.5 M to produce a reaction mixture. This initiated the precipitation of a solid portion suspected to contain impurities. About 15 mL of 10 M NaOH was added dropwise to the reaction mixture to bring the pH to between 7 and 8. This was done to avoid degradation of the fucoidan in the reaction mixture. The reaction mixture was brought to 0.5 M phosphate through the addition of phosphoric acid. This initiated flocculation of the suspended particulates and precipitated impurities via the action of calcium phosphate formed by the reaction of the calcium chloride with the phosphoric acid. The reaction mixture was centrifuged at 33,746 gravities for 5 minutes to separate a first purified/modified fucoidan in a supernatant solution from the flocculated impurities. The first purified/modified fucoidan was found to contain about 0.10% w/w total nitrogen. A portion of the first purified/modified fucoidan in the supernatant solution was further purified by diafiltration over a 100 kDa MWCO centrifugal filter against 6 diavolumes of 5 mM NaCl. The resulting first retentate purified/modified fucoidan was found to contain about 0.08% w/w total nitrogen.

A second portion of the first purified/modified fucoidan was further processed by adding 1 M sodium dodecyl sulfate solution as cellular disrupting agent to a concentration of 0.010 M. 10 M NaOH solution was added to a concentration of 0.26 M to render the mixture basic. The resulting reaction mixture was stirred for about 30 minutes at room temperature to obtain a cloudy light brown mixture.

After about 30 minutes, 45% w/v KOH solution was added to a concentration of about 0.04 M. The addition of potassium resulted in the precipitation of SDS and undesired impurities along with the SDS. 48% w/v aluminum sulfate solution was added to a concentration of about 0.06 M. The formation of aluminum hydroxide flocculated undesired impurities in the reaction mixture. Sodium sulfite solid was added and dissolved to a concentration of 0.02 M to quench potential oxidants in the reaction mixture.

The resulting reaction mixture was stored in a refrigerator for about 16 hours, followed by centrifugation at 33,746 gravities for 5 minutes to separate a second purified/modified fucoidan in a supernatant solution from the flocculated impurities. The second purified/modified fucoidan was found to contain about 0.06% w/w total nitrogen. A portion of the second purified/modified fucoidan was further processed by diafiltration over a 100 kDa MWCO centrifugal filter against 6 diavolumes of 5 mM NaCl to provide a second retentate purified/modified fucoidan. The resulting second retentate purified/modified fucoidan was found to contain about 0.03% w/w total nitrogen.

Example 13: Preparation of Five Purified/Modified Fucans

The methods discussed herein can be used, combined, modified and permuted in any manner to obtain purified/modified fucans. Five purified/modified fucans were prepared using a combination of chemically induced precipitation and diafiltration discussed in examples 4, 5, 6 and 10 to evaluate the efficacy of purified/modified fucans in medical and surgical applications. These 5 fucans are referred to as fucan 1 to fucan 5 herein. Fucan 1 and fucan 2 were produced at about a 2 kg scale using the methods discussed in example 4 and example 10. Fucan 3 and fucan 5 were produced at about a 30 g scale using the methods discussed in example 4 and example 10. Fucan 4 was produced at about a 1 kg scale using the methods discussed in example 5 and example 10. Fucans 1 to 5 were converted into solid purified/modified fucans by diafiltration against a low conductivity salt solution followed by lyophilization to obtain white solids. Two additional fucans were extracted from brown seaweed, herein referred to as fucan 6 and fucan 7. Fucan 6 was provided as a solid composition by FMC BioPolymer®. None of the processes discussed above were used in the production of fucan 6. Fucan 7 was extracted from brown seaweed by near boiling HCl. Some impurities were removed by selective precipitation using ethanol as the precipitant. After the selective precipitation, the fucan was collected as a solid composition by further precipitation of the fucan with ethanol, centrifugation and lyophilization. Fucan 7 was further treated with the method discussed in example 3, then dissolved in water and diafiltered against deionized water before being lyophilized to obtain fucan 7 as a solid composition. The fucose, galactose, sulfate and total counterion levels of fucan 1 to fucan 7 are determined as discussed in examples 14 and example 15 below. These fucans 1-7 are discussed further below, for example in example 16 and Table 6.

Example 14: Measurement of Corrected Fucose Content and Corrected Galactose Content of Fucan 1 to Fucan 7

Solid fucan compositions were dissolved in 72% w/w sulfuric acid at 40 mg/mL and incubated at 45° C. in a water bath for 30 minutes. The acid hydrolysate was then diluted to 4% w/w sulfuric acid in a high-pressure tube and incubated at 120° C. for 60 minutes. The resulting second acid hydrolysate was diluted to a 1/333 concentration with distilled water and run on high performance anionic exchange column chromatography set up with pulsed amperometry detection (HPAE-PAD). Separation of analytes was accomplished by running 10 mM NaOH eluent at 1.0 mL/minute using an isocratic pump.

The uncorrected fucose content of the fucans were determined by interpolation on a standard curve for fucose. The uncorrected galactose content of the fucans were determined by the method of standard addition. Corrected fucose content was determined by accounting for the addition of one molecule of water upon hydrolysis of a glycosidic bond, and accounting for the addition of two hydroxyl group upon hydrolysis of two sulfate-ester bonds pet fucose. Corrected galactose content was determined by accounting for the addition of one molecule of water upon hydrolysis of a glycosidic bond.

The results from this analysis are shown in table 5 below.

Example 15: Measurement of Total Sulfate Content, Total Counterion Content and Total Water Content of Fucan 1 to Fucan 7

Solid fucan compositions were dissolved in deionized water, hydrolyzed under acidic conditions and analyzed by ICP-MS for % w/w total sulfur and counterions content. Sulfur content was converted to sulfate content by multiplying the sulfur content by the molar ratio of sulfate to sulfur to obtain % w/w sulfate content of the purified/modified fucan. The counterions observed in the purified/modified fucan discussed herein included potassium and sodium counterions. The results from this analysis are shown in table 5 below.

The % w/w results for total corrected fucose, corrected galactose and sulfate are also shown in Table 5 below. The results for total fucose, galactose and sulfate are determined by adding the corrected fucose, corrected galactose and sulfate values together, a more detailed and complete calculation including aspects discussed above shown in equation 1 below. The total counterion content, is determined by adding together the total sodium and total potassium content.

$$\text{Total fucose, galactose and sulfate } (\%w/w \text{ of fucan}) = \\ \text{Total fucose hydrolysate } (\%w/w) * \frac{164.16 - 52.00}{164.16} + \\ \text{Total galactose hydrolysate } (\%w/w) * \frac{180.16 - 18.00}{180.16} + \\ \text{Total sulfur } (\%w/w) * \frac{96.06}{32.06}$$

Equation 1

TABLE 5

| | Fucose % w/w | Galactose % w/w | Sulfate % w/w | Total fucose, galactose and sulfate % w/w | Na % w/w | K % w/w | Total counterion content % w/w | Total fucose, galactose, sulfate and counterion content % w/w |
|---|---|---|---|---|---|---|---|---|
| Fucan 1 | 34.3 | 2.9 | 44.9 | 82.2 | 11.4 | 0.7 | 11.6 | 94.3 |
| Fucan 2 | 34.7 | 2.5 | 41.7 | 78.9 | 9.8 | 0.8 | 10.6 | 89.5 |
| Fucan 3 | 35.3 | 2.3 | 41.7 | 79.2 | 9.4 | 1.6 | 10.9 | 90.2 |
| Fucan 4 | 31.1 | 3.4 | 51.3 | 84.0 | 7.8 | 5.3 | 13.0 | 98.8 |
| Fucan 5 | 32.7 | 3.0 | 40.6 | 76.3 | 11.0 | 1.3 | 12.3 | 88.6 |
| Fucan 6 | 18.6 | 1.4 | 11.4 | 31.3 | 8.3 | 1.4 | 9.7 | 41.0 |
| Fucan 7 | 23.3 | 5.9 | 11.4 | 40.6 | 2.6 | 0.9 | 3.5 | 44.1 |

Table 5 demonstrates that purified/modified fucans with less than about 12%, 10%, 9%, 8%, 7%, 6%, 5%, 4%, 3% or 2% w/w impurities can be prepared using methods discussed herein.

Table 5 further demonstrates purified/modified fucans with a total galactose, fucose and sulfate content of between about 77% w/w and about 87% w/w have been produced.

Table 5 further demonstrates purified/modified fucans with a total counterion content between about 9% w/w and about 14% w/w of the fucan.

The total water content of fucan 1, fucan 3, fucan 4 and fucan 5 were determined by loss on drying (LOD) at 104° C. The total water content were determined to be 3.8%, 2.4%, 3.2% and 4.7% w/w of the respective purified/modified fucans.

Example 16: Measurement of Molecular Weight Distributions of Fucan 3 and Fucan 4

Gel permeation chromatography (GPC) was used to evaluate the molecular weight distributions obtained for the purified/modified fucans fucan 3 and fucan 4. There are a large number of different parameters, columns and standards available for use in gel permeation chromatography, resulting in a variety of instrumentation set-ups available for the analysis of molecular weight. For molecular weight determinations herein, the GPC were conducted using the following parameters: The mobile phase was 0.1M sodium nitrate run at 0.6 mL/min. The column compartment and detector were at 30° C. A Waters 2414 refractive index detector was used for detection.

Suitable GPC columns include GPC columns compatible with aqueous solvents, for example columns packed with at least one of sulfonated styrene-divinylbenzene, NH-functionalized acrylate copolymer network, modified silica and hydroxylated polymethacrylate-based gel. For the analyses herein, three columns were used in series, comprising one 40 mm long guard column with an inner diameter (ID) of 6 mm packed with 6 μm particle size hydroxylated polymethacrylate-based gel, followed by a first 300 mm analytical GPC column with a 7.8 mm ID packed with 12 μm particle size hydroxylated polymethacrylate-based gel that has an exclusion limit of about 7,000 kDa and an effective molecular weight range of between about 50 kDa and about 5,000 kDa, followed by a second 300 mm analytical GPC column with a 7.8 mm ID packed with 10 μm particle size hydroxylated polymethacrylate-based gel that has an exclusion limit of about 7,000 kDa and an effective molecular weight range of between about 1 kDa and about 6,000 kDa. The total effective molecular weight range of the column set up was between about 1 kDa and about 6,000 kDa. An example of this column set up can be Ultrahydrogel® guard-Ultrahydrogel® 2000-Ultrahydrogel® Linear columns connected in series.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

Results in table 6 below contain abbreviations used for certain characteristics of a molecular weight distribution. Gel permeation chromatography is denoted by GPC, peak molecular weight is denoted by PMW, weight average molecular weight is denoted by WAMW, number average molecular weight is denoted by NAMW, percentage distribution is denoted by % dist. and molecular weight is denoted by MW.

TABLE 6

Molecular weight distribution characteristics of two modified fucans

|  | PMW (kDa) | WAMW (kDa) | NAMW (kDa) | % dist. >100 kDa | % dist. >200 kDa | % dist. >500 kDa |
|---|---|---|---|---|---|---|
| Fucan 3 | 690.98 | 1166.60 | 443.37 | 97.77 | 90.06 | 63.89 |
| Fucan 4 | 686.21 | 1876.74 | 524.89 | 98.37 | 92.97 | 69.90 |

Example 17: Preparation of Highly Purified Fucan Composition by Drying

About 100 mg of Fucan 1 was placed in a crucible. The crucible containing Fucan 1 was placed in an oven at 105° C. for 30 minutes to produce a further-purified fucan composition, hereinafter called Fucan 1'. The crucible containing the further-purified Fucan 1' composition was removed from the oven and placed in a desiccator. The further-purified Fucan 1' composition is analyzed under a moisture free atmosphere for total fucose and galactose by HPAE-PAD and for total sulfur and counterion content by ICP-MS, and is found to contain a total fucose, galactose, sulfate and counterion content of over 99.9% w/w, in other words, less than 0.1% impurities.

Example 18: Preparation of Highly Purified Fucan Composition by Drying

About 600 mg of Fucan 1 was placed on an aluminum pan in an Ohaus MB 90 moisture analyzer instrument. The instrument was programmed to heat Fucan 1 at 105° C. for 30 minutes to produce a further-purified Fucan 1" composition. The further-purified Fucan 1" composition was removed from the instrument and placed in a desiccator. The sample is analyzed under a moisture free atmosphere for total fucose and galactose by HPAE-PAD and for total sulfur and counterion content by ICP-MS, and is found to contain a total fucose, galactose, sulfate and counterion content of over 99.9% w/w, less than 0.1% impurities.

Example 19: Uterine Horn Fibrous Adhesion Treated with Fucan 1

To determine the efficacy of the purified/modified fucan 1 in inhibiting surgical adhesions, the following double uterine horn (DUH) surgeries were performed on both horns of a total of two New Zealand White rabbits. Prior to surgery, the rabbits were weighed and then prepared for surgery by premedication with ketamine and xylazine.

Fucoidan solution was prepared at 0.33 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. A minimal amount of fucoidan solution was applied directly to the injured uterine horns and sidewall areas. The damaged uterine horns and abdominal wall were placed next to each other and stabilized with sutures. 15 mL/kg fucoidan solution per rabbit weight was applied to the abdominal cavity before the incision was closed. Adhesion was evaluated two weeks after the surgery. Length of the uterine horn adhesion was measured with a ruler. The uterine horn adhesion coverage percentage, being the length of the adhesion as a percentage of the total damaged uterine horn length was calculated as:

$$\text{Adhesion coverage (\%)} = 100 \times \text{uterine horn adhesion length} \div \text{total damaged uterine horn length} \quad \text{Equation 2:}$$

The same surgical method was applied to New Zealand White rabbits, receiving 15 mL/kg of Lactated Ringer's Injection USP (LRS) instead of fucoidan solution as a control group. The control group receiving LRS was determined to have a 63% adhesion coverage using equation 2. Table 7 shows the results obtained using the method described above for fucan 2, being a representative example of a purified/modified fucan. The results in the table below are shown as the reduction in adhesion coverage relative to the control group.

Table 7 provides the results of treating six uterine horn with fucan 1.

TABLE 7

Reduction in rabbit uterine horn adhesion using fucan 1

|  | Dose (mg/kg) | Number of Uterine Horns | % Reduction in uterine horn adhesion coverage vs. control |
|---|---|---|---|
| Fucan 1 | 5 | 6 | 100% |

As can be seen from the results of Table 7, the purified/modified fucans discussed herein can be used to successfully treat post-surgical uterine horn adhesions.

Example 20: Uterine Horn Fibrous Adhesion Treated with Fucan 4

To determine the efficacy of the purified/modified fucan 4 in inhibiting surgical adhesions, the following double uterine horn (DUH) surgeries were performed on both horns of a total of four New Zealand White rabbits. Prior to surgery, the rabbits were weighed and then prepared for surgery by premedication with ketamine and xylazine.

Fucoidan solution was prepared at 3.75 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns were also scraped. 4 mL of fucoidan solution was applied directly to the left injured uterine horn and sidewall area and 4 mL of fucoidan solution was applied directly to the right injured uterine horn and sidewall area. The damaged uterine horns and abdominal wall were placed next to each other and stabilized with sutures. A drainage tube was positioned in the peritoneal cavity before the incision was closed. The drainage tube is removed 48 hours post-surgery. Adhesion was evaluated two weeks after the surgery. Length of the uterine horn adhesion was measured with a ruler. The uterine horn adhesion coverage was calculated using equation 2.

The same surgical method was applied to 3 New Zealand White rabbits, receiving 4 mL per side of Lactated Ringer's Injection USP (LRS) instead of fucoidan solution as a control group. The control group receiving LRS was determined to have a 73% adhesion coverage using equation 2. Table 8 shows the results obtained using the method described above for fucan 4, being a representative example of a purified/modified fucan. The results in the table below are shown as the reduction in adhesion coverage relative to the control group.

Table 8 provides the result of treating eight uterine horns with fucan 4.

TABLE 8

Reduction in rabbit uterine horn adhesion using fucan 4

| Dose (mg/kg) | Number of Uterine Horns | % Reduction in uterine horn adhesion coverage vs. control |
|---|---|---|
| Fucan 4    9.8 | 8 | 92.9% (i.e., 92.9% reduction in fibrous adhesions compared to control) |

As can be seen from the results of Table 8, the purified/modified fucans can be used to successfully treat post-surgical uterine horn adhesions.

Example 21: Uterine Horn Fibrous Adhesion Treated with Fucan 6

To determine the efficacy of the purified/modified fucan 6 in inhibiting surgical adhesions, the following double uterine horn (DUH) surgeries were performed on both horns of a total of four New Zealand White rabbits. Prior to surgery, the rabbits were weighed and then prepared for surgery by premedication with ketamine and xylazine.

Fucoidan solution was prepared at 0.33 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. About 15 mL/kg fucoidan solution per rabbit weight was applied to the abdominal cavity before the incision was closed. Adhesion was evaluated two weeks after the surgery. Three rabbits were evaluated at each fucoidan concentration prepared. Length of the uterine horn adhesion was measured with a ruler. The uterine horn adhesion length was calculated using equation 2.

The same surgical method was applied to 4 New Zealand White rabbits, receiving about 15 mL/kg of control Lactated Ringer's Injection USP (LRS) instead of fucoidan solution. The control group receiving LRS was determined to have a 71% adhesion coverage using equation 2. Table 9 shows the results obtained using the method discussed above for fucan 6. The results in the table below are shown as the reduction in adhesion coverage relative to the control group.

Table 9 provides the result of treating eight uterine horns with fucan 6.

TABLE 9

Increase in rabbit uterine horn adhesion using fucan 9 relative to control LRS

| Dose (mg/kg) | Number of Uterine Horns | % Reduction in uterine horn adhesion coverage vs. control |
|---|---|---|
| Fucan 6    5 | 8 | −18% (i.e., 18% increase in fibrous adhesions compared to control) |

As can be seen from the results of Table 9, fucan 6 prepared using known methods and having a total non-fucan content of greater than 50% w/w of the fucan was not efficacious in the treatment of fibrous adhesions.

Example 22: Uterine Horn Fibrous Adhesion Treated with Fucan 7

To determine the efficacy of the purified/modified fucan 7 in inhibiting surgical adhesions, the following double uterine horn (DUH) surgeries were performed on both horns of a total of four New Zealand White rabbits. Prior to surgery, the rabbits were weighed and then prepared for surgery by premedication with ketamine and xylazine.

Fucoidan solution was prepared at 0.33 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. About 15 mL/kg fucoidan solution per rabbit weight was applied to the abdominal cavity before the incision was closed. Adhesion was evaluated two weeks after the surgery. Three rabbits were evaluated at each fucoidan concentration prepared. Length of the uterine horn adhesion was measured with a ruler. The uterine horn adhesion length was calculated using equation 2.

The same surgical method was applied to 4 New Zealand White rabbits, receiving about 15 mL/kg of control Lactated Ringer's Injection USP (LRS) instead of fucoidan solution. The control group receiving LRS was determined to have a 76% adhesion coverage using equation 2. Table 10 shows the results obtained using the method discussed above for fucan 7. The results in the table below are shown as the reduction in adhesion coverage relative to the control group.

Table 10 provides the result of treating eight uterine horns with fucan 7.

TABLE 10

Decrease in rabbit uterine horn adhesion using fucan 7 relative to control LRS

| Dose (mg/kg) | Number of Uterine Horns | % Reduction in uterine horn adhesion coverage vs. control |
|---|---|---|
| Fucan 7    5 | 8 | 3.7% (i.e., 3.7% reduction in fibrous adhesions compared to control) |

As can be seen from the results of Table 10, fucan 7 prepared using known methods and having a total non-fucan content of greater than 50% w/w of the fucan is not efficacious in the treatment of fibrous adhesions.

Example 23: Uterine Horn Fibrous Adhesion Treated with Fucan 4

To determine the efficacy of the purified/modified fucan 4 in inhibiting surgical adhesions, the following double uterine horn (DUH) surgeries were performed on both horns of a total of three New Zealand White rabbits. Prior to surgery, the rabbits were weighed and then prepared for surgery by premedication with ketamine and xylazine.

Fucoidan solution was prepared at 5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. The top third and the bottom third of the muscle incision was closed and 5 mL/kg fucoidan solution per rabbit weight was applied to the abdominal cavity. The muscle incision was temporarily closed and the fucoidan solution left in the abdominal cavity for 30 minutes. The muscle incision was reopened and the abdominal cavity was flushed with 10 mL/kg LRS. The majority of the fluid in the abdominal cavity was suctioned out before the incision was closed. Adhesion formation was evaluated two weeks after the surgery. Length of the uterine horn adhesion was measured with a ruler. The uterine horn adhesion coverage percentage, being the length of the adhesion as a percentage of the total damaged uterine horn length was calculated using equation 2.

Table 11 shows the results obtained using the method discussed above for fucan 4, being a representative example of a purified/modified fucan. The results in the table below are shown as the mean adhesion length across the 6 uterine horns scored.

Table 11 provides the results of treating six uterine horns with fucan 4.

TABLE 11

Adhesion length using fucan 4

| | Dose (mg/kg) | Number of Uterine Horns | Mean % adhesion length |
|---|---|---|---|
| Fucan 4 | 25 | 6 | 0% (i.e., no adhesions were found) |

As can be seen from the results of Table 11, purified/modified fucans can be used to successfully inhibit, prevent, remove, reduce, or otherwise treat post-surgical uterine horn adhesions.

Example 24: Uterine Horn Fibrous Adhesion Treated with a Purified/Modified Fucan Composition To determine the efficacy of a purified/modified fucan composition comprising a total fucose, galactose, sulfate and counterions of 92% w/w in inhibiting surgical adhesions, the following double uterine horn (DUH) surgeries were performed on both horns of a total of twenty New Zealand White rabbits. Prior to surgery, the rabbits were weighed and then prepared for surgery by premedication with midazolam and dexmeditomidine.

Fucoidan solution was prepared at each concentration of 0.02 mg/mL, 0.1 mg/mL, 0.5 mg/mL, or 2.5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. About 2 mL/kg fucoidan solution per rabbit weight was applied to the abdominal cavity before the incision was closed. Adhesion was evaluated two weeks after the surgery. Five rabbits were treated and evaluated for each fucoidan concentration prepared. Length of the uterine horn adhesion was measured with a ruler. The uterine horn adhesion length was calculated using equation 2.

The same surgical method was applied to 5 additional New Zealand White rabbits for control, each receiving about 2 mL/kg of control Lactated Ringer's Injection USP (LRS) instead of fucoidan solution. The control group receiving LRS was determined to have a 100% adhesion coverage using equation 2. Table 12 shows the results obtained using the method discussed above for the purified/modified fucan composition at different concentrations and dosages (in total forty uterine horns were treated, 10 each for each concentration of the purified/modified fucan composition); the results are shown as the reduction in adhesion coverage relative to the control group.

TABLE 12

Decrease in rabbit uterine horn adhesion using a purified/modified fucan composition relative to control LRS

| Concentration (mg/mL) | Dose (mg/kg) | Number of Uterine Horns | % Reduction in uterine horn adhesion coverage vs. control |
|---|---|---|---|
| 0.02 | 0.04 | 10 | 10% (i.e., 10% decrease in fibrous adhesions compared to control) |
| 0.1 | 0.2 | 10 | 30% (i.e., 30% decrease in fibrous adhesions compared to control) |
| 0.5 | 1 | 10 | 71% (i.e., 71% decrease in fibrous adhesions compared to control) |
| 2.5 | 5 | 10 | 95% (i.e., 95% decrease in fibrous adhesions compared to control) |

As can be seen from the results of Table 12, purified/modified fucan compositions can be used to successfully inhibit, prevent, remove, reduce, or otherwise treat post-surgical uterine horn adhesions.

REFERENCE NUMERALS LIST

1200 Cationic content modification system
1202 Input supply line
1204 Pre-filter
1206 Cationic content modification system output valve
1208 Cationic content modification system output line
1210 Tangential flow filtration (TFF) filter
1212 TFF supply line
1214 TFF input pump
1216 Fucan container
1217 TFF retentate valve
1218 TFF retentate return line
1219 TFF permeate output line
1220 First diafiltration solution container
1224 First diafiltration solution valve 1225 First diafiltration solution supply line
1230 Second diafiltration solution container
1234 Second diafiltration solution valve
1235 Second diafiltration solution supply line All terms used herein are used in accordance with their ordinary meanings unless the context or definition clearly indicates otherwise. Also unless expressly indicated otherwise, in this disclosure the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates otherwise.

Unless otherwise stated, adjectives herein such as "substantially" and "about" that modify a condition or relationship characteristic of a feature or features of an embodiment, indicate that the condition or characteristic is defined to within tolerances that are acceptable for operation of the embodiment for an application for which it is intended.

The scope of the present methods, compositions, systems, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications can be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion and figures herein.

What is claimed is:

1. A purified and modified, medically acceptable fucan composition consisting of at least about 96% w/w purified and modified fucans and no more than about 4% non-fucan components or compounds or substances, wherein the purified and modified fucan must have fucose, sulfate and counterions, and may further consist of galactose, glucose, rhamnose, mannose, xylose and glucuronic acid.

2. The purified and modified, medically acceptable fucan composition of claim 1 wherein the non-fucan components comprise water.

3. The purified and modified, medically acceptable fucan composition of claim 1 wherein the purified and modified, medically acceptable fucan composition consists of the purified and modified fucan and no more than about 3% of the non-fucan components.

4. The purified and modified, medically acceptable fucan composition of claim 1 wherein the purified and modified, medically acceptable fucan composition consists of the purified and modified fucan and no more than about 2% of the non-fucan components.

5. The purified and modified, medically acceptable fucan composition of claim 1 wherein the purified and modified, medically acceptable fucan composition consists of the purified and modified fucan and no more than about 1% of the non-fucan components.

6. The purified and modified, medically acceptable fucan composition of claim 1 wherein the purified and modified, medically acceptable fucan composition consists of the purified and modified fucan and no more than about 0.1% of the non-fucan components.

7. The purified and modified, medically acceptable fucan composition of any one of claim 1, 3, or 5 wherein the fucose content of the purified and modified fucan is greater than 25% w/w.

8. The purified and modified, medically acceptable fucan composition of any one of claim 1, 3 or 5 wherein the galactose content of the purified and modified fucan is less than 10% w/w.

9. The purified and modified, medically acceptable fucan composition of any one of claim 1, 3, or 5 wherein the total counterion content of the purified and modified fucan is less than 17% w/w.

10. The purified and modified, medically acceptable fucan composition of any one of claim 1, 3 or 5 wherein the counterion is a pharmaceutically acceptable counterion.

11. The purified and modified, medically acceptable fucan composition of claim 10 wherein the pharmaceutically acceptable counterion consists essentially of at least one of sodium and potassium.

12. The purified and modified, medically acceptable fucan composition of any one of claim 1, 3 or 5 wherein the purified and modified fucan has a molecular weight distribution wherein at least 60% w/w of the distribution is greater than 100 kDa when measured using an aqueous gel permeation chromatography set up consisting essentially of:
one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;
a refractive index detector at about 30° C.;
0.1M sodium nitrate mobile phase run at 0.6 mL/min; and
quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa.

13. The purified and modified, medically acceptable fucan composition of claim 12, wherein the purified and modified fucan has a molecular weight distribution wherein at least 92% w/w of the distribution is greater than 100 kDa.

14. The purified and modified, medically acceptable fucan composition of claim 12, wherein the purified and modified fucan has a weight average molecular weight greater than 100 kDa.

15. The purified and modified, medically acceptable fucan composition of any one of claim 1, 3, or 5, wherein the purified and modified fucan has a sulfation level of between about 20% w/w and 60% w/w.

16. The purified and modified, medically acceptable fucan composition of any one of claim 1, 3 or 5, wherein the purified and modified fucan has a total carbohydrate content between 27% w/w and 80% w/w.

17. The purified and modified, medically acceptable fucan composition of claim 16, wherein the purified and modified fucan has a total of glucuronic acid, mannose, rhamnose, glucose and xylose content as a percentage of the total carbohydrate content below about 12% w/w.

18. The purified and modified, medically acceptable fucan composition of any one of claim 1, 3 or 5 wherein the purified and modified, medically acceptable fucan composition when dissolved in water at a concentration of 50 mg/mL has a viscosity of between about 4 cP and 50 cP.

19. The purified and modified, medically acceptable fucan composition of any one of claim 1, 3 or 5 wherein the purified and modified, medically acceptable fucan composition is a white solid.

20. The purified and modified, medically acceptable fucan composition of any one of claim 1, 3 or 5 wherein the purified and modified, medically acceptable fucan composition when dissolved in water at a concentration from 1 mg/mL through 100 mg/mL forms a solution that is clear and colorless.

21. The purified and modified, medically acceptable fucan composition of any one of claim 1, 3 or 5 wherein the purified and modified, medically acceptable fucan comprises less than 5% w/w acetyl content.

22. The purified and modified, medically acceptable fucan composition of any one of claim 1, 3 or 5 wherein the purified and modified fucan comprises an acetyl content of substantially 0% w/w when measured by 2D 1H-13C heteronuclear multiple quantum coherence at 70° C. with solvent signal suppression on a 600 MHz spectrometer equipped with 5-mm cold probe, in the range from 10-30 ppm in the carbon dimension, in 8 increments of 256-512 scans each.

23. A purified and modified, medically acceptable composition comprising a therapeutically effective amount of the purified and modified, medically acceptable fucan composition of any one of claim 1, 3 or 5.

24. A medical composition comprising between about 0.02 mg/mL and 100 mg/mL of the purified and modified, medically acceptable fucan composition of any one of claim 1, 3 or 5 in a medically acceptable liquid, wherein the medical composition is configured and composed to treat a disease or condition in an animal.

25. The medical composition of claim 24 wherein the disease or condition is a fibrous adhesion.

26. The purified and modified, medically acceptable fucan composition of claim 10 wherein the pharmaceutically acceptable counterion consists of at least one of calcium and magnesium.

27. The purified and modified, medically acceptable fucan composition of claim 12 wherein the purified and modified fucan has a sulfation level of between about 20% w/w and 60% w/w.

28. The purified and modified, medically acceptable fucan composition of claim 12, wherein the purified and modified fucan has a total carbohydrate content between 27% w/w and 80% w/w.

29. The purified and modified, medically acceptable fucan composition of claim 15, wherein the purified and modified fucan has a total carbohydrate content between 27% w/w and 80% w/w.

30. The purified and modified, medically acceptable fucan composition of claim 27, wherein the purified and modified fucan has a total carbohydrate content between 27% w/w and 80% w/w.

31. The purified and modified, medically acceptable fucan composition of claim 12 wherein the purified and modified fucan comprises less than 5% w/w acetyl content.

32. The purified and modified, medically acceptable fucan composition of claim 15 wherein the purified and modified fucan comprises less than 5% w/w acetyl content.

33. The purified and modified, medically acceptable fucan composition of claim 27 wherein the purified and modified fucan comprises less than 5% w/w acetyl content.

34. The purified and modified, medically acceptable fucan composition of claim 30 wherein the purified and modified fucan comprises less than 5% w/w acetyl content.

* * * * *